(12) United States Patent
Franer et al.

(10) Patent No.: US 8,012,128 B2
(45) Date of Patent: Sep. 6, 2011

(54) BUTTON LATCHING SYSTEM FOR A TROCAR

(75) Inventors: Paul T. Franer, Cincinnati, OH (US); Mark S. Zeiner, Mason, OH (US); Mark L. Holthaus, Fairfield, OH (US)

(73) Assignee: Ethicon Endo-Surgery Inc., Cincinnati, OH (US)

( * ) Notice: Subject to any disclaimer, the term of this patent is extended or adjusted under 35 U.S.C. 154(b) by 1659 days.

(21) Appl. No.: 11/119,491

(22) Filed: May 2, 2005
(Under 37 CFR 1.47)

(65) Prior Publication Data

US 2006/0264992 A1 Nov. 23, 2006
US 2010/0160938 A9 Jun. 24, 2010

Related U.S. Application Data

(63) Continuation-in-part of application No. 10/943,220, filed on Sep. 17, 2004, now Pat. No. 7,785,294.

(60) Provisional application No. 60/506,782, filed on Sep. 30, 2003.

(51) Int. Cl.
*A61M 5/178* (2006.01)
(52) U.S. Cl. .................................. 604/164.07
(58) Field of Classification Search ..... 604/158–170.03, 604/264
See application file for complete search history.

(56) References Cited

U.S. PATENT DOCUMENTS

| | | |
|---|---|---|
| 3,504,699 A | 4/1970 | Grise |
| 3,773,233 A | 11/1973 | Souza |
| 4,436,519 A | 3/1984 | O'Neill |
| 4,601,710 A | 7/1986 | Moll |
| 4,610,665 A | 9/1986 | Matsumoto et al. |
| 4,654,030 A | 3/1987 | Moll |
| 4,896,986 A * | 1/1990 | Terayama ..................... 403/14 |
| 4,902,280 A | 2/1990 | Lander |
| 4,931,042 A | 6/1990 | Holmes et al. |
| 4,932,633 A | 6/1990 | Johnson et al. |
| 5,030,206 A | 7/1991 | Lander |
| 5,053,013 A | 10/1991 | Ensminger et al. |
| 5,104,383 A | 4/1992 | Shichman |
| 5,203,773 A | 4/1993 | Green |
| 5,209,737 A | 5/1993 | Ritchart et al. |
| 5,211,634 A | 5/1993 | Vaillancourt |
| 5,246,425 A | 9/1993 | Hunsberger et al. |
| 5,300,033 A | 4/1994 | Miller |
| 5,308,336 A | 5/1994 | Hart et al. |
| 5,324,270 A | 6/1994 | Kayan et al. |
| 5,366,445 A | 11/1994 | Haber et al. |
| 5,385,552 A | 1/1995 | Haber et al. |

(Continued)

FOREIGN PATENT DOCUMENTS

EP 0339945 11/1989

(Continued)

*Primary Examiner* — Nicholas D Lucchesi
*Assistant Examiner* — Nathan R Price
(74) *Attorney, Agent, or Firm* — Welsh Flaxman & Gitler LLC

(57) ABSTRACT

A trocar housing for a trocar assembly includes a first housing member selectively coupled to a second housing member, wherein the first and second housing members include aligned apertures shaped and dimensioned for passage of an instrument therethrough. A button latch mechanism selectively couples the first housing member and the second housing member, the button latch mechanism including a latching member which slides about a central axis of the first and second housing members for selectively coupling the first and second housing members.

8 Claims, 16 Drawing Sheets

U.S. PATENT DOCUMENTS

| | | | |
|---|---|---|---|
| 5,385,553 A | 1/1995 | Hart et al. |
| 5,441,041 A | 8/1995 | Sauer et al. |
| 5,456,284 A | 10/1995 | Ryan et al. |
| 5,467,762 A | 11/1995 | Sauer et al. |
| 5,534,009 A | 7/1996 | Lander |
| 5,542,931 A | 8/1996 | Gravener et al. |
| 5,569,160 A | 10/1996 | Sauer et al. |
| 5,578,016 A | 11/1996 | Zinger |
| 5,584,850 A | 12/1996 | Hart et al. |
| 5,603,702 A | 2/1997 | Smith et al. |
| 5,643,301 A | 7/1997 | Mollenauer |
| 5,807,338 A | 9/1998 | Smith et al. |
| 5,843,000 A * | 12/1998 | Nishioka et al. ............. 600/566 |
| 5,895,377 A | 4/1999 | Smith et al. |
| 6,024,729 A | 2/2000 | Dehdashtian et al. |
| 6,086,603 A | 7/2000 | Termin et al. |
| 6,277,100 B1 | 8/2001 | Raulerson et al. |
| 6,302,852 B1 | 10/2001 | Fleming, III et al. |
| 6,352,520 B1 | 3/2002 | Miyazaki |
| 6,569,120 B1 | 5/2003 | Green et al. |
| 6,613,063 B1 | 9/2003 | Hunsberger |
| 6,685,630 B2 | 2/2004 | Sauer et al. |
| 6,702,787 B2 | 3/2004 | Racenet et al. |
| 2002/0007153 A1 | 1/2002 | Wells et al. |
| 2002/0010425 A1 | 1/2002 | Guo et al. |
| 2004/0049173 A1 | 3/2004 | White et al. |
| 2004/0064100 A1 | 4/2004 | Smith |
| 2004/0147949 A1 | 7/2004 | Stellon et al. |
| 2004/0220602 A1 | 11/2004 | Deng et al. |
| 2004/0236347 A1 | 11/2004 | Karasawa |
| 2005/0010238 A1 | 1/2005 | Potter et al. |
| 2005/0070850 A1 * | 3/2005 | Albrecht .................. 604/167.03 |

FOREIGN PATENT DOCUMENTS

| | | |
|---|---|---|
| EP | 0567142 | 10/1993 |
| EP | 0568383 | 11/1993 |
| EP | 0696459 | 2/1996 |
| EP | 1520540 | 4/2005 |
| WO | WO 94/03232 | 2/1994 |
| WO | WO 00/35529 | 6/2000 |
| WO | WO 2004/033004 | 4/2004 |

* cited by examiner

BUTTON LATCHING SYSTEM FOR A TROCAR

CROSS REFERENCE TO RELATED APPLICATIONS

This application is a continuation-in-part of U.S. patent application Ser. No. 10/943,220, entitled, "ROTATIONAL LATCHING SYSTEM FOR TROCAR", filed Sep. 17, 2004, now U.S. Pat. No. 7,785,294, which claims the benefit of U.S. Provisional Patent Application Ser. No. 60/506,782, entitled "ROTATIONAL LATCHING SYSTEM FOR TROCAR", filed Sep. 30, 2003.

BACKGROUND OF THE INVENTION

1. Field of the Invention

The invention relates to trocar assemblies. More particularly, the invention relates to a button latch mechanism for selectively securing first and second housing members of a trocar assembly with one-hand actuation thereof for selective separation of the first and second housing members.

2. Description of the Prior Art

Endoscopic surgical procedures have been widely accepted in the medical field since they provide a lower risk and a faster recovery period for the patient. Consequently, many minimally-invasive surgical instruments have been developed. In the midst of these newly emerging tools, a trocar assembly plays a crucial role. A trocar assembly is a surgical instrument that is used to gain access to a body cavity. A trocar assembly generally comprises two major components, a trocar sleeve, composed of a trocar housing and a trocar cannula, and a trocar obturator. The trocar cannula, having the trocar obturator inserted therethrough, is directed through the skin to access a body cavity. Once the body cavity is accessed, laparoscopic or arthroscopic surgery and endoscopic procedures may be performed. In order to penetrate the skin, the distal end of the trocar cannula is placed against the skin that has been previously cut with a scalpel. The trocar obturator is then used to penetrate the skin and access the body cavity. By applying pressure against the proximal end of the trocar obturator, the sharp point of the trocar obturator is forced through the skin until it enters the body cavity. The trocar cannula is inserted through the perforation made by the trocar obturator and the trocar obturator is withdrawn, leaving the trocar cannula as an access way to the body cavity.

The proximal end portion of the trocar cannula is typically joined to a trocar housing that defines a chamber having an open distal end portion in communication with the interior lumen defined by the trocar cannula. A trocar obturator, or other elongated surgical instruments axially extend into and are withdrawn from the trocar cannula through the proximal end portion of the chamber defined by the trocar housing.

Many trocar housings are formed with first and second housing members respectively housing a proximal seal assembly and a duckbill seal assembly. The housing members are selectively coupled to facilitate various surgical procedures. For example, it is often desirable to remove the first housing member during the removal of a specimen. The removal of the first housing member allows the specimen to pass through only the duckbill seal assembly, instead of passing through both the duckbill seal assembly and the proximal seal assembly. This provides for easier specimen removal and less trauma to the specimen during the removal process.

However, prior trocar housings utilize complicated and unreliable mechanisms for securing the first and second housing members. As such, a need exists for a trocar housing offering a convenient and reliable mechanism for connecting first and second housing members. The present invention provides such a mechanism while allowing for one-handed operation.

SUMMARY OF THE INVENTION

It is, therefore, an object of the present invention to provide a trocar housing for a trocar assembly. The trocar housing includes a first housing member selectively coupled to a second housing member, wherein the first and second housing members include aligned apertures shaped and dimensioned for passage of an instrument therethrough. A button latch mechanism selectively couples the first housing member and the second housing member, the button latch mechanism including a latching member which slides about a central axis of the first and second housing members for selectively coupling the first and second housing members.

It is also an object of the present invention to provide a trocar housing for a trocar assembly. The trocar housing includes a first housing member selectively coupled to a second housing member, wherein the first and second housing members include aligned apertures shaped and dimensioned for passage of an instrument therethrough. A button latch mechanism selectively couples the first housing member and the second housing member. The button latch mechanism includes a latching member which slides about a central axis of the first and second housing members for selectively coupling the first and second housing members, at least one arm extending from the first housing member and an aperture formed in the second housing member through which the arm is passed upon engagement of the first and second housing members, the aperture being only slightly larger than the arm to prevent bending of the arm.

It is another object of the present invention to provide a trocar housing for a trocar assembly. The trocar housing includes a first housing member selectively coupled to a second housing member, wherein the first and second housing members include aligned apertures shaped and dimensioned for passage of an instrument therethrough. A button latch mechanism selectively couples the first housing member and the second housing member, the button latch mechanism including a resilient latching ring which slides about a central axis of the first and second housing members for selectively coupling the first and second housing members.

Other objects and advantages of the present invention will become apparent from the following detailed description when viewed in conjunction with the accompanying drawings, which set forth certain embodiments of the invention.

DESCRIPTION OF THE PREFERRED EMBODIMENTS

Figure 1:
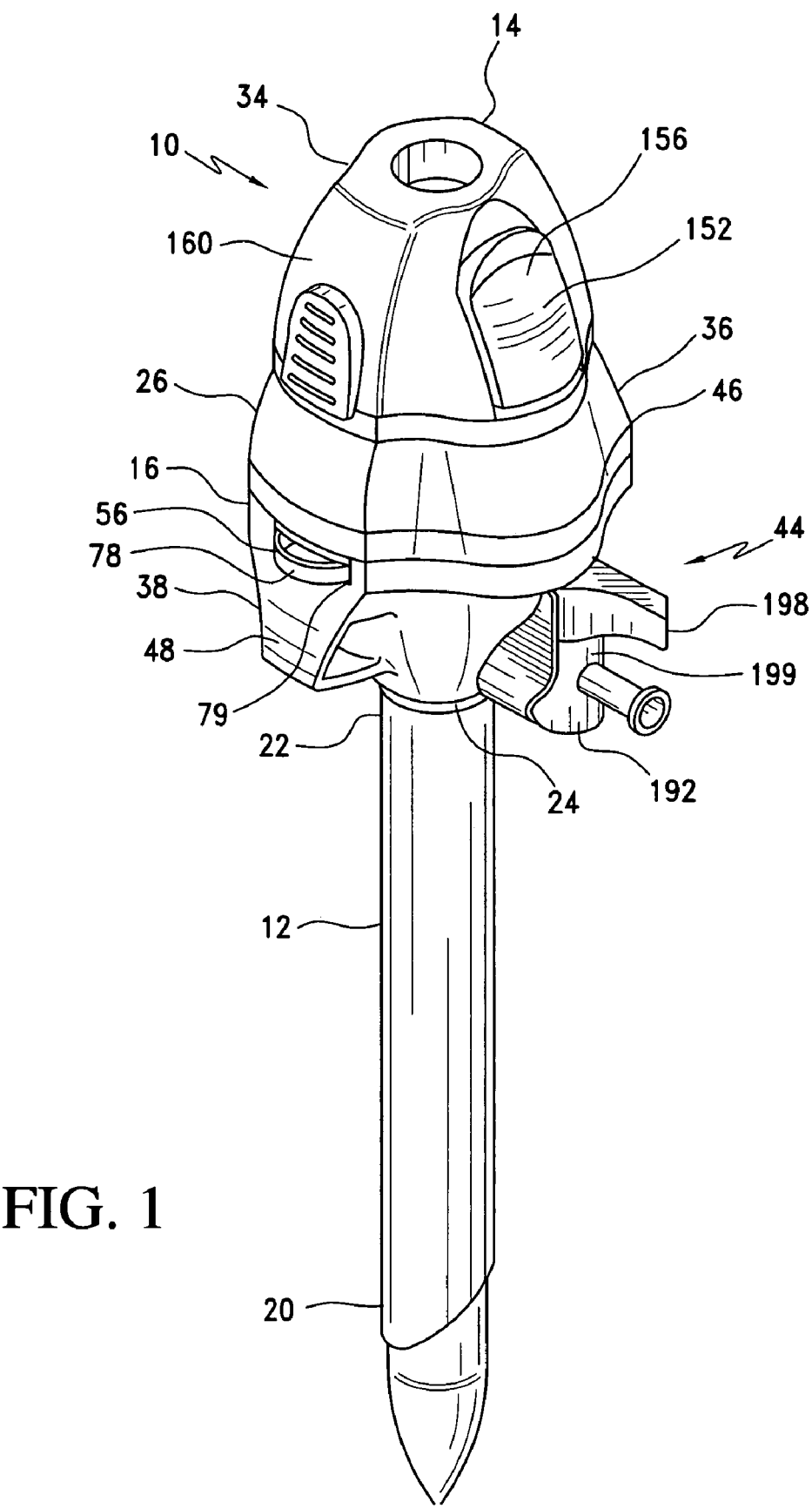
FIG. 1 is a perspective view of a trocar assembly in accordance with the present invention.
Figure 2:
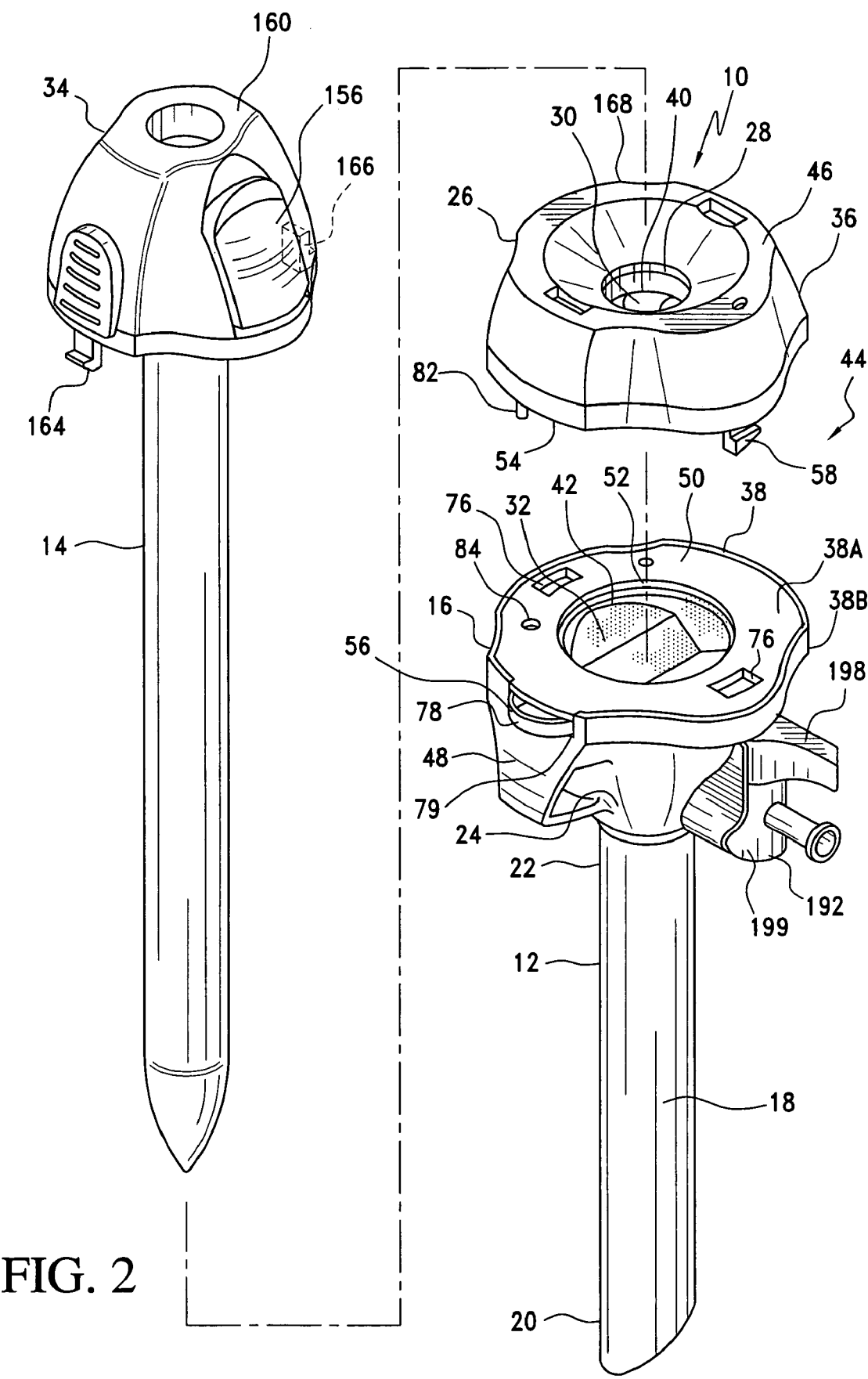
FIG. 2 is an exploded view of the trocar assembly shown in FIG. 1.

The detailed embodiments of the present invention are disclosed herein. It should be understood, however, that the disclosed embodiments are merely exemplary of the invention, which may be embodied in various forms. Therefore, the details disclosed herein are not to be interpreted as limiting, but merely as the basis for the claims and as a basis for teaching one skilled in the art how to make and/or use the invention.

A button latch mechanism 56 in accordance with the present invention is disclosed. As will be discussed below in greater detail, the button latch mechanism 56 allows for selective coupling of first and second housing members for added versatility in the use of a trocar assembly. As those skilled in the art will certainly appreciate, the present rotary latch mechanism is adapted for use with a variety of trocar assemblies without departing from the spirit of the present invention.

Referring to FIGS. 1 to 5, the trocar assembly 10 generally includes a trocar cannula 12, a trocar obturator 14, and a trocar housing (or handle) 16. The trocar cannula 12 defines an interior lumen 18 having an open distal end portion 20 and an open proximal end portion 22. The proximal end portion 22 extends into and is mounted in the distal end portion 24 of trocar housing 16. The trocar housing 16 has an open proximal end portion 26 that defines an opening 28. The opening 28 is provided with a proximal seal assembly 30 constructed in accordance with the present invention and described in detail hereinbelow. The opening 28 is further provided with a duckbill seal assembly 32 positioned beneath the proximal seal assembly 28. While the present seal assembly is disclosed as a proximal seal assembly forming part of a dual sealing system, the present seal assembly may be utilized in a single seal system without departing from the spirit of the present invention.

In general, the trocar sleeve 44 is composed of a trocar cannula 12 and a trocar housing 16. The trocar housing 16 includes a first housing member 36 and a second housing member 38. The second housing member 38 is ultimately composed of a second housing member cover 38a and a second housing member base 38b. Although, the housing 16 is disclosed as two components it is contemplated that a single component could be used without departing from the spirit of the present invention. The two component housing shown, aids in removal of specimens.

The trocar obturator 14 is slidable in and removable from within the trocar cannula 12 and is inserted into the trocar housing 16 and the trocar cannula 12 through the proximal seal assembly 30, the duckbill seal assembly 32 and the opening 28 of the trocar housing 16. An obturator handle 34 is provided at the proximal end of the trocar obturator 14 and a point or blade (not shown) is formed at the distal end thereof. As is well known in the art, the proximal seal assembly 30 cooperates with the exterior of the instruments (for example, trocar obturators and other tools adapted for use in conjunction with trocar based procedures) extending through the trocar sleeve 44 to sealingly engage the exterior surface thereof and thereby preclude the passage of fluids through the trocar housing 16.

Button Latching System

With regard to the trocar housing 16 and with reference to FIGS. 1 to 5 and 22 to 29, the trocar housing 16 is constructed of a first housing member 36 and a second housing member 38 which are selectively coupled for reasons that will be discussed below in greater detail. The first and second housing members 36, 38 include aligned apertures 40, 42 shaped and dimensioned for the receipt of instruments that are selectively passed through the trocar housing 16.

As those skilled in the art will certainly appreciate, it is important that the first and second housing members 36, 38 remain securely attached during the insertion of the trocar sleeve 44 into the abdominal wall, as well as during the normal course of a procedure. However, it is also desirable, in some cases, to remove the first housing member 36. For example, the first housing member 36 must be removed during the removal of a specimen from the abdominal cavity. The removal of the first housing member 36 allows the specimen to pass through only the duckbill seal assembly 32, instead of passing through both the duckbill seal assembly 32 and the tauter proximal seal assembly 30. This provides for easier specimen removal and less trauma to the specimen during the removal process. Importantly, the button latch mechanism 56 allows for one-handed operation.

The first housing member 36 supports the proximal seal assembly 30 and sits atop the second housing member 38 in which the duckbill seal assembly 32 is mounted. The first housing member 36 includes an aperture 40 extending therethrough. The proximal seal assembly 30 is positioned within the aperture 40 of the first housing member 36.

As to the second housing member 38, the second housing member 38 includes an aperture 42 extending therethrough. The duckbill seal assembly 32 is positioned within the aperture 42 of the second housing member 38 beneath the top surface 50 of the second housing member 38. In fact, and for reasons which will be discussed below in greater detail, the peripheral rim 52 of the duckbill seal assembly 32 is positioned directly beneath the top surface 50 of the second housing member 38 for engagement with the lower surface 54 of the first housing member 36.

The preferred embodiment of the button latch mechanism 56 will be disclosed first. Connection of the first housing member 36 to the second housing member 38 is facilitated by a button latch mechanism 56. In particular, the first housing member 36 includes downwardly extending arms called detainment legs 58. Each of the detainment legs 58 includes a downwardly facing camming surface 60 and an outwardly facing latching surface 62. Although only one detainment leg 58 would be necessary for proper operation in accordance with the present invention, it should be understood that more may be added for additional security of the attachment between the second and first housing members 36, 38. In fact, and in accordance with a preferred embodiment of the present invention, two detainment legs 58 are used in the preferred embodiment.

The second housing member 38 includes a button flex ring 64 with detainment pins 66 along its inner circumference for respectively engaging the respective detainment legs 58 of the first housing member 36. The button flex ring 64 is axially aligned with the central axis of the trocar sleeve 44 and lies in an annular groove 68 around the perimeter of the duckbill seal assembly 32. The button flex ring 64 is composed of a stiff, yet flexible, material molded in a bowed configuration that naturally expands outward. Although the button flex ring 64 is molded into a "sprung open" position, notches 306 along the inner circumference of the ring 64 give it flexibility as opposed to the ring being permanently molded. This allows the button flex ring 64 to flex, or begin to close, when pressure is applied via the button 78. Because of these flex properties of the button flex ring 64, no spring is needed to load the button latch mechanism 56, as the stored energy lies in the flex ring 64 itself, rather than a spring; that is, the button flex ring 64 is generally C-shaped and is positioned within the second housing member 38 such that a spring force is maintained within the button flex ring 64. Along the inner circumference of the button flex ring 64, notches 306 allow the button flex ring 64 to flex when pressure is applied. Along the inner circumference of the button flex ring 64 protrude detainment pins 66. It should also be noted that notches 306 may also lay along the outer perimeter of the button flex ring 64 in order to instill flexibility within the ring.

The button flex ring 64 allows the attachment of the first housing member 36 to the second housing member 38. The detainment pins 66 include upwardly facing camming surfaces 72 that interface with downwardly facing camming surfaces 60 of the detainment legs 58 of the first housing member 36.

The detainment pins 66 each include an upwardly facing camming surface 72 shaped and dimensioned to respectively engage the camming surfaces 60 of the detainment legs 58. Similarly, the detainment pins 66 include inwardly facing latching surfaces 74 shaped and dimensioned for engaging the outwardly facing latching surfaces 62 of the detainment legs 58.

In practice, latching of the first and second housing members 36, 38 is achieved by passing the detainment legs 58 through holes 76 formed in the top surface 50 of the second housing member 38. As the detainment legs 58 extend through the respective holes 76 adjacent the detainment pins 66 of the button flex ring 64, the camming surfaces 60 of the respective detainment leg 58 engage the camming surfaces 72 of the detainment pins 66. This engagement causes the button flex ring 64 to move circumferentially about the vertical axis of the trocar housing 16 from the position of the button 78 as the button flex ring 64 slides along the annular groove 68 until the two ends of the button flex ring 64 near each other. This permits the detainment legs 58 to extend past the latch members 74. Again, this flexibility is provided by the natural molding of the button flex ring 64.

Once the detainment legs 58 move past the detainment pins 66, the natural outward bowing of the button flex ring 64 causes the button flex ring 64 to return to its original position and the outwardly facing latching surfaces 62 of the first housing member 36 to engage the inwardly facing latching surfaces 74 of the second housing member 38 to securely couple the first housing member 36 to the second housing member 38. The first and second housing members 36, 38 are selectively disengaged through the pushing of the button 78 located on the button flex ring 64. Pushing the button 78 causes the button flex ring 64 to move circumferentially to the source of pressure as it slides along the annular groove 68 until the ends of the button flex ring 64 near each other. This moves the latching members 74 out of engagement with the detainment legs 58, and the two housing members may be separated.

The top surface 50 of the second housing member 38 includes holes 76 allowing the detainment legs 58 of the first housing member 36 to pass through with only a small amount of clearance. This limited clearance allows for very little movement of the detainment legs 58 in the plane of the holes 76 and limits the possible bending thereof. Therefore, when the first housing member 36 is latched to the second housing member 38, the only means of forceful disassembly of the first and second housing members 36, 38 is by shearing the first and second detainment legs 58 themselves or by pure tension on the detainment legs 58 themselves. The detainment legs 58 cannot bend out of the way or slip due to the size of the holes 76. This creates a very secure attachment.

Figure 29:
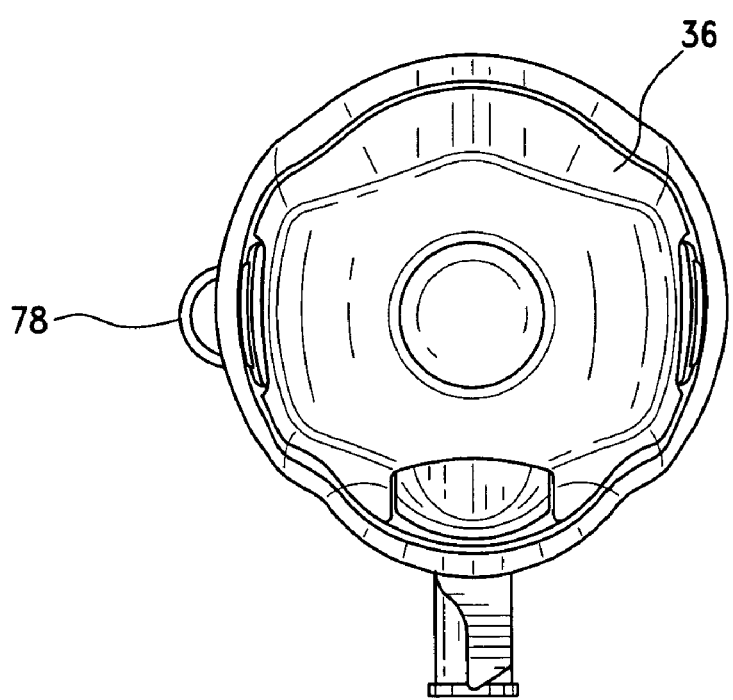
FIG. 29 is a top view of the trocar, which illustrates the accessibility of the button.

The trocar housing 16 is disassembled by pushing the button 78 inwardly toward the central axis of the trocar, causing sliding of the button flex ring 64 about the central axis of the trocar sleeve 44, in a manner overcoming the natural force at which the molding button flex ring is bowing out. The button 78 is accessible to the surgeon through a slot 79 in the side of the trocar housing 16 as shown in FIG. 29. When the button 78 is pressed, the latching members 74 of the button flex ring 64 slide past the detainment legs 58, and the first housing member 36 is released from the second housing member 38. This embodiment is not limiting, as features may be altered while still remaining within the spirit of the invention. For example, the camming surfaces of the button flex ring 64 may lie on top of the ring itself or outside of the ring while still keeping to the spirit of the invention. An alternate embodiment could involve detainment legs containing inwardly facing latching surfaces, while the detainment pins of the button flex ring contain outwardly facing latching surfaces. The spirit of the invention would remain intact.

As discussed above, the button latch mechanism 56 utilized in connecting the first housing member 36 to the second housing member 38 offers a wide variety of advantages. In particular, the button latch design allows the first housing member 36 to be rigidly attached to the second housing member 38 with no chance of the latches becoming accidentally disengaged, while allowing very easy detachment of the first housing member 36. In fact, the holes 76 through which the detainment legs 58 of the first housing member 36 pass through disallows any chance of the detainment legs 58 bending out of the way. Finally, the button latch mechanism 56 is easily manipulated with one hand.

Although the embodiment described above discloses the flex ring positioned within the second housing member, it is contemplated the structure could be reversed, that is, the flex ring positioned within the first housing member and the second housing member provided with detainment legs.

Proper alignment between the first and second housing members 36, 38 is achieved by the provision of an alignment pin 82 extending downwardly from the lower surface 54 of the first housing member 36 and a mating hole 84 shaped and dimensioned for receiving the alignment pin 82 formed along the top surface 50 of the second housing member 38. The provision of the alignment pin 82 and the mating hole 84 ensures that the first and second housing members 36, 38 may only be assembled in the desired configuration. Optionally, a second pin may be provided to prevent the opposite latch from engaging. This is an integral part of the design as it is intended for safety. The trocar obturator 14 can only be attached to the first housing member 36 in one configuration and the first housing member 36 can only be attached to the second housing member 38 in one configuration.

As discussed above, the button latch mechanism 56 utilized in connecting the first housing member 36 to the second housing member 38 offers a wide variety of advantages. In particular, the button latch design allows the first housing member 36 to be rigidly attached to the second housing member 38 with no chance of the latches accidentally disengaging, while allowing very easy detachment of the first housing member 36. In fact, the holes 76 through which the detainment legs 58 of the first housing member 36 pass through disallows any chance of the detainment legs 58 bending out of the way. Finally, the button latch mechanism 56 is easily manipulated with one hand.

Reinforced Seal Assembly

Referring to FIGS. 6 to 10, the proximal seal assembly 30 is disclosed. The seal assembly generally includes a cap 86, a crown 88, bellows 90 used for radial seal movement, a female retaining ring 92, a protector 94, a plurality of reinforced seal segments 96 making up a seal body 98, a male retaining ring 100 and a bottom body 102. The reinforced seal segments 96 are positioned as described below in greater detail and mounted between the retaining rings 92, 100 for creating a seal assembly 30 in accordance with the present invention.

More particularly, and with reference to FIGS. 7 to 10, a reinforced seal segment 96 is shown. As is described in greater detail below, the proximal seal assembly 30 employs a plurality of reinforced seal segments 96 in creating a complete seal body 98. Each of the reinforced seal segments 96 is in the form of a partial cone, in particular, a cone extending about approximately 225 degrees. While the partial cone shape in accordance with a preferred embodiment of the present invention employs partial cones extending about approximately 225 degrees, partial cones of other shapes may be employed without departing from the sprit of the present invention. Although cone shaped seal segments are disclosed in accordance with a preferred embodiment, flat seal segments could be employed without departing from the spirit of the present invention.

In practice, a series of reinforced seal segments 96 are utilized in the creation of a seal body 98 through which an instrument may be inserted. In accordance with a preferred embodiment of the present invention, four reinforced seal segments 96 are aligned and successively shifted 90 degrees relative to each other. The seal segments 96 are arranged in a "woven" manner. That is, each seal segment 96 includes a first side 104 and second side 106, and the first side 104 of each seal segment 96 is placed atop the second side 106 of the adjacent seal segment 96 to create a "woven" assembly of seal segments 96.

The reinforced seal segments 96 are then bound together along their peripheral edges 108 to the male and female retaining rings 94, 100 to create a complete seal body 98. As a result of the partial cone shape of the reinforced seal segments 96 and the relative rotation thereof, the bound seal segments 96 create a seal body 98 wherein the individual seal segments 96 are pushed outwardly upon the insertion of an instrument to create an opening for the passage of instruments and resilient move inwardly to close the opening upon the removal of instruments. The typical deformation of the reinforced seal segment 96 is shown with reference to FIG. 3. The deformation is shown with the insertion of an instrument therethrough.

As mentioned above, each of the reinforced seal segments 96 is generally in the form of a cone with a portion of the cone cut away. The reinforced seal segment 96 includes a peripheral edge 108 secured to a central seal member 110. The peripheral edge 108 is substantially flat, lying in the same plane, while the central seal member 110 is formed in the shape of a section of a cone.

The central seal member 110 is enhanced through the inclusion of a reinforcement pad 112 at a central position on the reinforced seal segment 96. That is, the reinforcement pad 112 is positioned between the peripheral edge and the free edge of the central seal member 110. More particularly, the reinforcement pad 112 is positioned at the tip of the cone defined by the central seal member 110 with edges of the reinforcement pad 112 being aligned with the free edge of the central seal member 110 at the tip of the cone.

Figure 7:
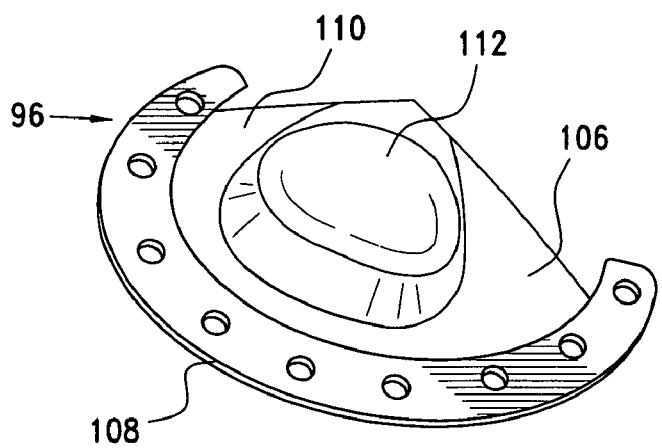
FIG. 7 is a bottom perspective view of a seal segment.
Figure 8:
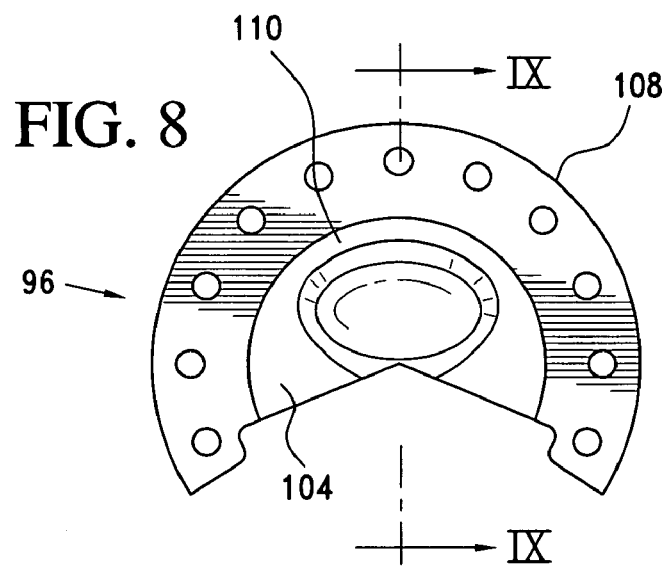
FIG. 8 is a top view of a seal segment.
Figure 9:
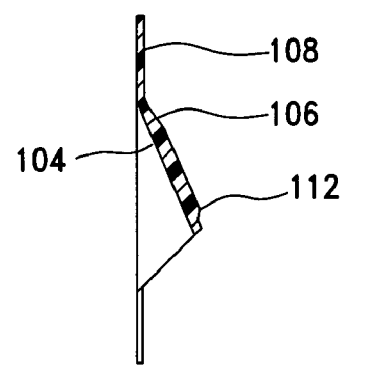
FIG. 9 is a cross sectional view along the line IX-IX in FIG. 8.
Figure 10:
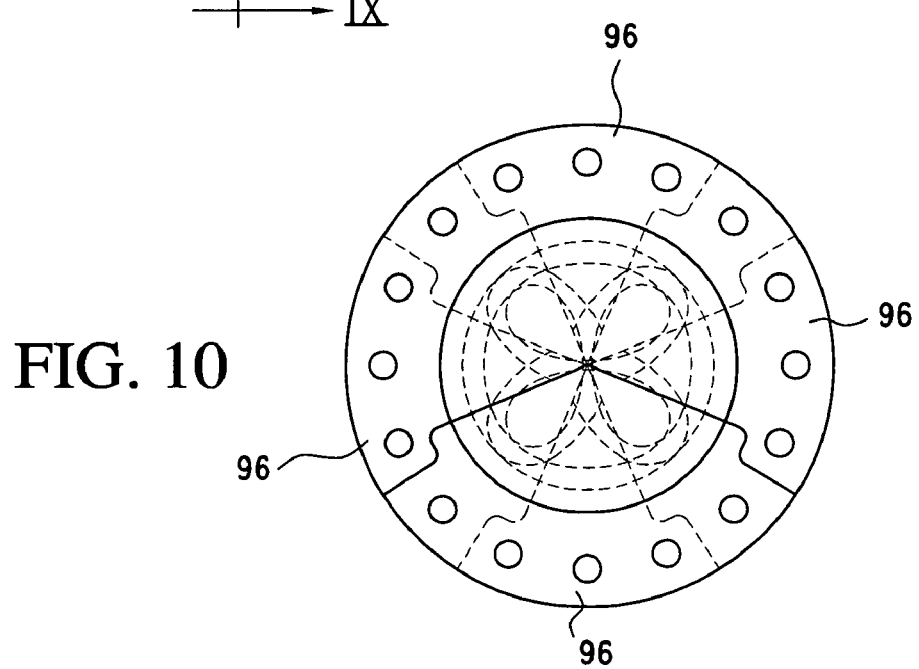
FIG. 10 is a seal body composed of four seal segments as shown in FIGS. 7, 8 and 9.
Figure 11:
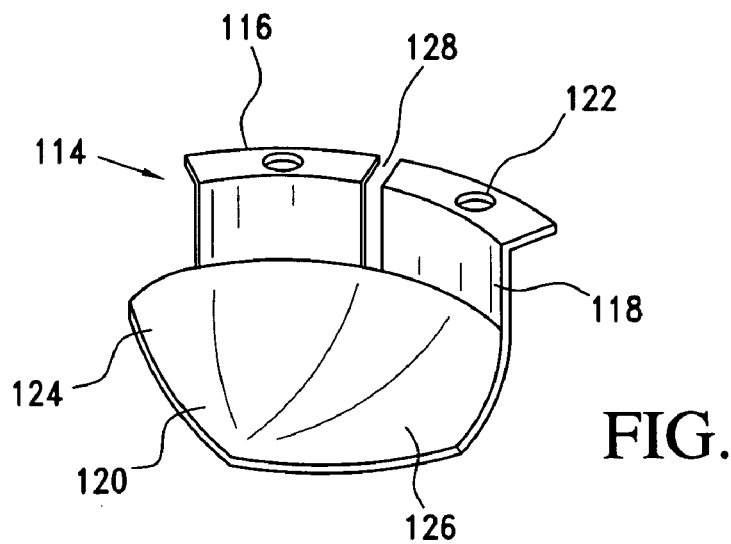
FIG. 11 is a top perspective view of a protector segment.
Figure 12:
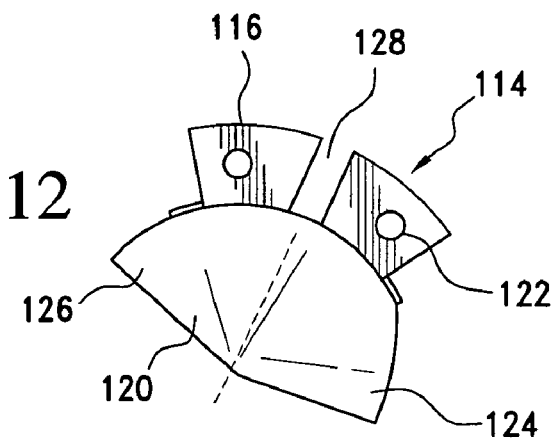
FIG. 12 is a bottom view of a protector segment.

As shown in FIG. 7, and in accordance with a preferred embodiment of the present invention, the reinforcement pad 112 is general formed in a triangular configuration along the center of the arc defined by the reinforced seal segment 96. In particular, the reinforcement pad 112 occupies an arc of approximately 90 degrees along the central seal member 110. As those skilled in the art will certainly appreciate, the shape and size of the reinforcement pad 112 may be varied to suit specific needs without departing from the spirit of the present invention. However, the reinforcement pad 112 should be shaped and dimensioned to cover an area that is intended for contact with instruments being passed through the trocar assembly 10.

The reinforcement pad 112 is located on a portion of the central seal member 110 that is most likely to have direct contact with surgical instruments as they are inserted within the trocar cannula 12. In accordance with a preferred embodiment of the present invention, the reinforcement pad 112 is centrally located, as most surgical instruments will be inserted through the center of the trocar housing 16 and the trocar cannula 12.

Woven Seal Protector

Figure 13:
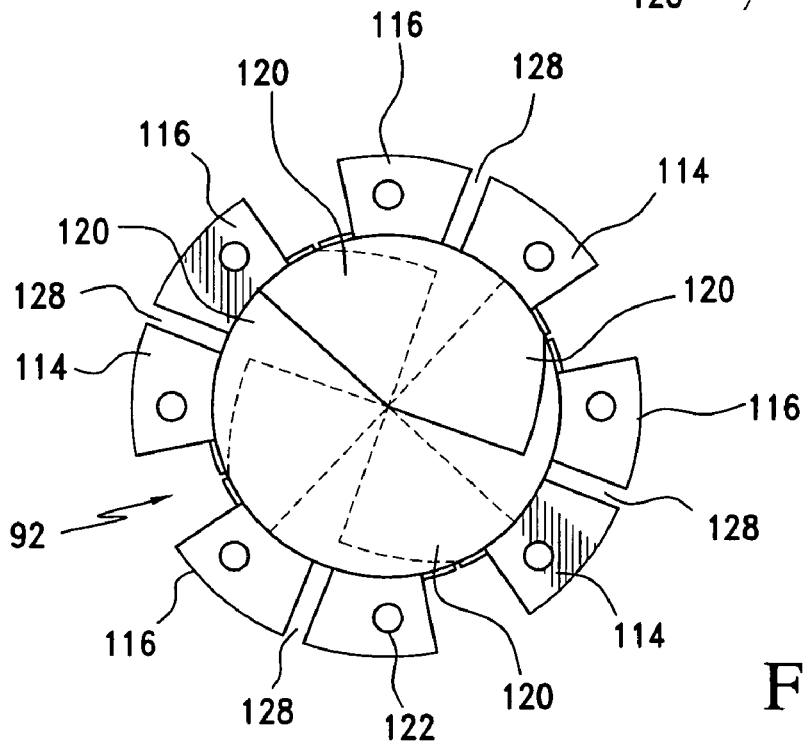
FIG. 13 is protector composed of four protector segments as shown in FIGS. 11 and 12.

Although the seal body 98 is formed with reinforcement pads 112 as described above it is still desirable to provide the proximal seal assembly 30 with a protector 92, as best shown in FIG. 13. The protector 92 in accordance with a preferred embodiment of the present invention is positioned directly above the seal body 98. With reference to FIGS. 6 and 11-13, the protector 92 is composed of multiple overlapping protector segments 114 assembled in a woven arrangement to provide a complete protector 92. By forming the protector 92 in a woven arrangement, additional protector material is added (as a result of the overlapping arrangement) such that additional surface area of the seal body 98 may be protected as the protector segments 114 separate as an instrument is inserted into the seal.

As the present proximal seal assembly 30 has a small central opening which expands in a reliable and convenient manner, the protector 92 must be formulated to close gaps between protector segments 114 as an instrument is passed through the protector 92 and the seal body 98. This requires the addition of material along the opening of the protector 92.

Each protector segment 114 is semicircular when viewed from above and is generally in the form of a partial cone. Each of these protector segments 114 include a substantially round peripheral edge 116, a support wall 118 extending from the peripheral edge 116 and a cone shaped protector member 120. The cone shaped protector member 120 opposite the support wall 118 and the peripheral edge 116 defines straight shaped edge 121.

In accordance with a preferred embodiment of the present invention, the cone shaped protector member 120 spans an arc of approximately 180 degrees, while the support wall 118 and the peripheral edge 116 span an arc of approximately 120 degrees along the center of the cone shaped protector member 120. As will be discussed below in greater detail, the limited arc spanned by the peripheral edge 116 and the support wall 118 reduces undesirable forces as instruments are moved past the proximal seal assembly 30.

The outer peripheral edge 116 is adapted for positioning within the first housing member 36. The outer peripheral edge 116 further includes a series of apertures 122 that function as a means of attachment for the protector segments 114. As will be apparent based upon the following disclosure, the use of multiple protector segments 114 defining an arc of approximately 180 degrees results in a reduction in hoop stresses by providing a protector 92 composed of a series of protector segments 114 which readily bend in and out radially as instruments are inserted therethrough.

Each protector segment 114 includes a first section 124 and a second section 126 defining opposite sides of the protector segment 114. The four individual protector segments 114 are combined in a woven arrangement to create a complete protector 92 that fully protects the underlying seal body 98. That is, the protector 92 is assembled by placing the first section 124 of a first protector segment 114 upon the second section 126 of a second protector segment 114. The first section 124 of the second protector segment 114 is subsequently placed upon the second section 126 of a third protector segment 114, the first section 124 of the third protector segment 114 is placed upon the second section 126 of a fourth protector segment 114 and the first section 124 of the fourth protector segment 114 is placed upon the second section 126 of the first protector segment 114 like one folds the final flap of a box lid.

The protector segments 114 are ultimately held together through the application of the crown 88 and female retaining ring 94. Retaining members are well known to those skilled in the art and a variety of retaining members may be employed within the spirit of the present invention.

As those skilled in the art will readily appreciate, movement of the cone shaped protector members 120 relative to the peripheral edge 116 and the support wall 118 is subject to resistance based upon the various orientations of the connected components. As such, the cone shaped protector members 120 might be susceptible to buckling as instruments are moved through the proximal seal assembly 30.

This resistance to movement is minimized due to the limited arc of the peripheral edge 116 and the support wall 118 as discussed above. In addition, the resistance is further minimized by forming a central slot 128 with the peripheral edge 116 and/or the support wall 118. This slot 128 functions to reduce buckling as the protector members 120 may move the same distance with less resistance.

By weaving the protector 92 additional material may be added to each protector segment 114 while still allowing the distal end of the protector 92 to fit into the apex of the cone shaped seal body 98. This is accomplished by having the extra material added to the protector segments 114 wrap behind the protector segment 114 adjacent thereto. This extra material allows for improved coverage of the seal body 98, especially when instruments are inserted at an angle relative to the proximal seal assembly 30. Finally, weaving of the protector 92 has minimal, if any effects on the instrument drag force as it is moved in and out of the proximal seal assembly 30. This is a result of the fact that the protector segments 114 move easily relative to each other.

In practice, and due to the extra material added to each protector segment 114, as an instrument is inserted into the protector 92, the protector segments 114 spread, exposing the additional protector material positioned behind adjacent protector segments 114. This additional material continues to cover the seal body 98 as the protector segments 114 bend relative to one another. The less seal body 98 material exposed to the inserted instrument, the better the protection offered by the present protector 92. While the present protector 92 offers good seal protection, additional protector segments 114 can be added although they might cause an increase in the instrument drag forces. This may be balanced, however, by thinning the protector segments 114 to make them more flexible or by adding lubricant to the protector segments 114 and/or the seal body 98.

Duckbill Seal Assembly

Figure 14:
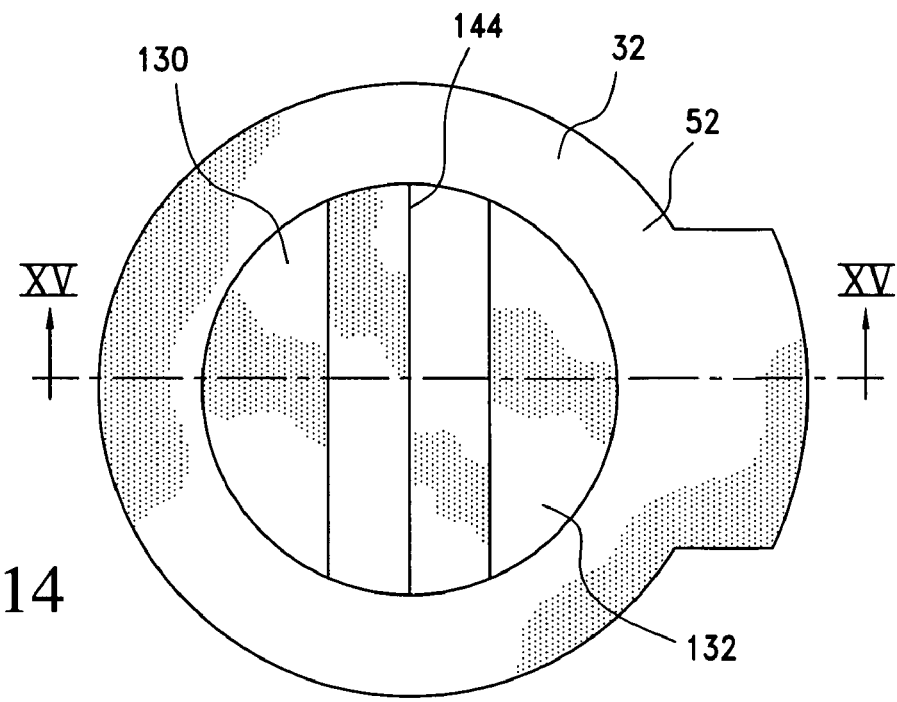
FIG. 14 is a top perspective view of a duckbill seal assembly in accordance with the present invention.
Figure 15:
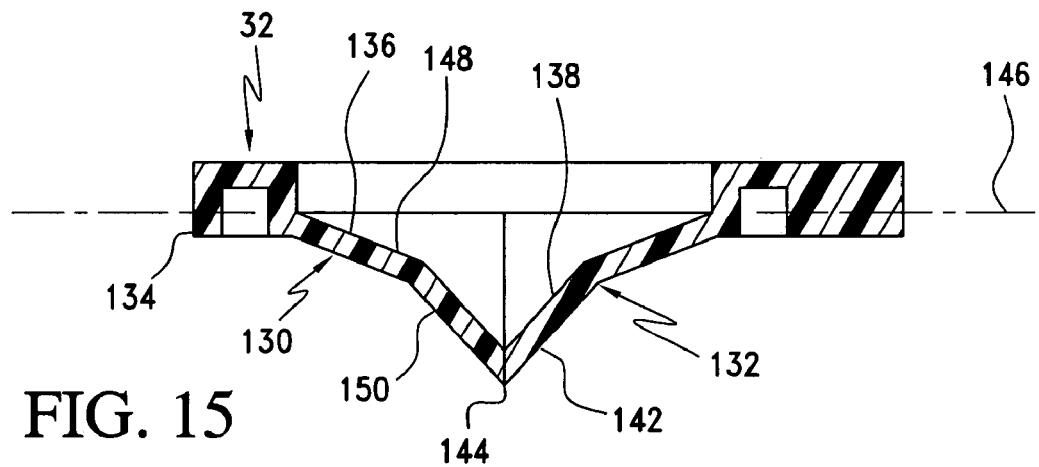
FIG. 15 is a cross sectional view along the line XV-XV of FIG. 14.
Figure 16:
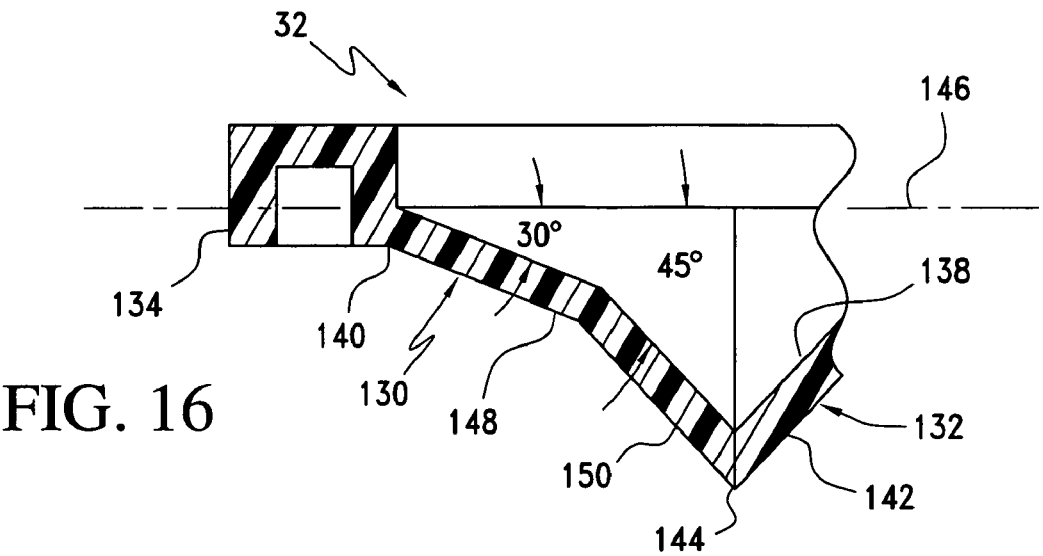
FIG. 16 is a partial cross sectional view along the line XV-XV of FIG. 14.
Figure 17:
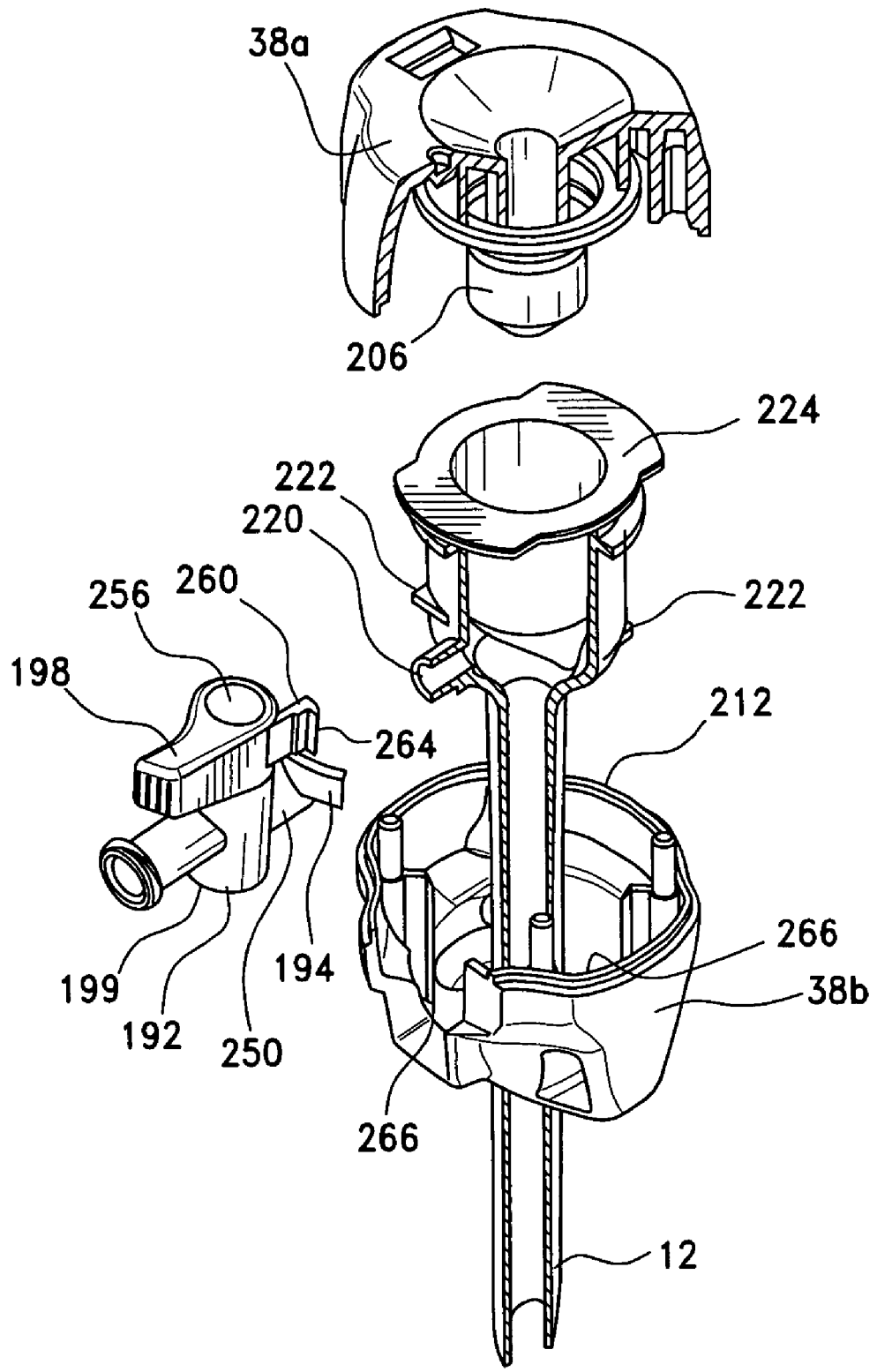
FIG. 17 is an exploded view of the trocar sleeve in accordance with the present invention.
Figure 18:
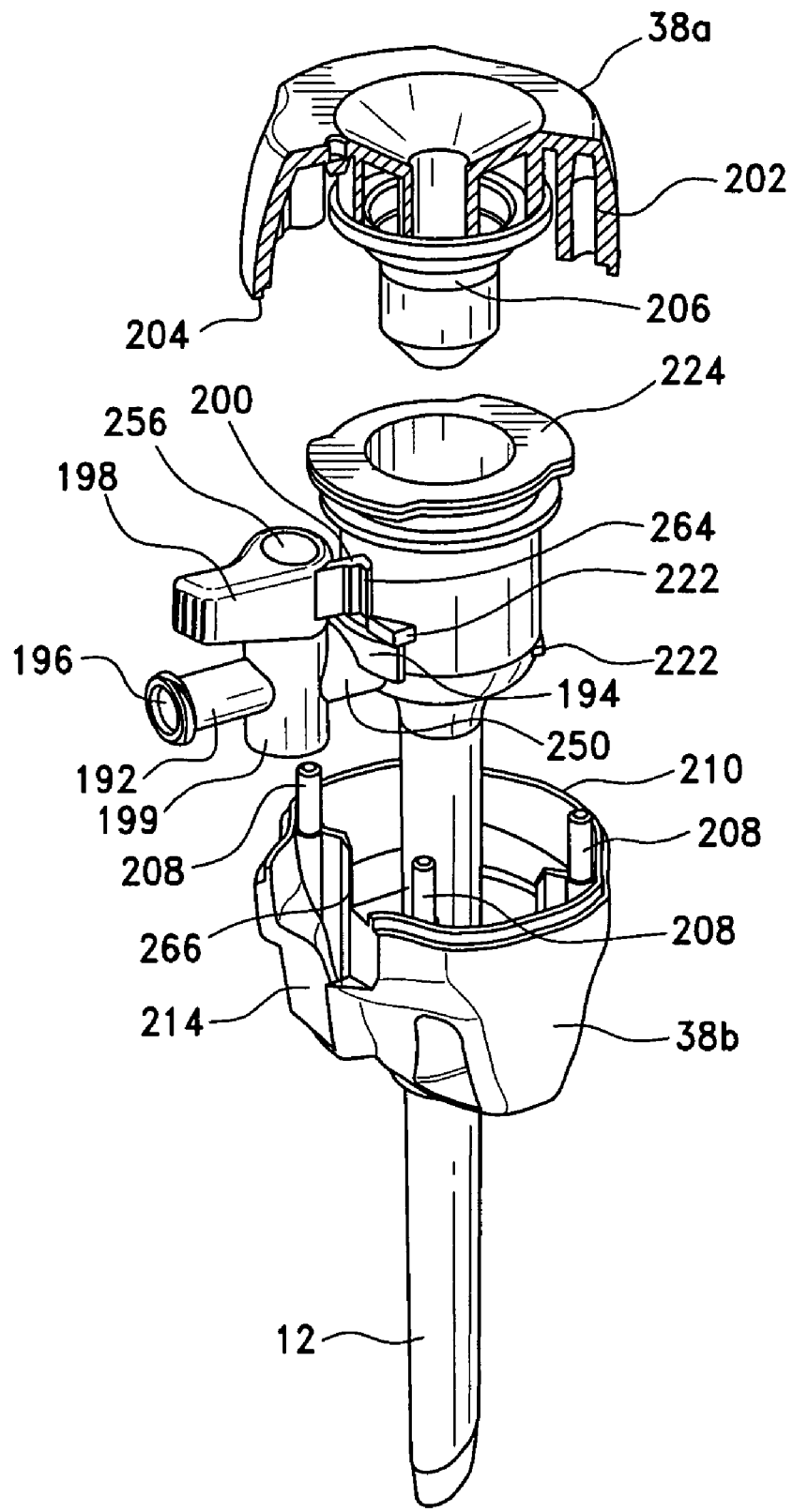
FIG. 18 is a further exploded view of the trocar sleeve in accordance with the present invention.
Figure 19:
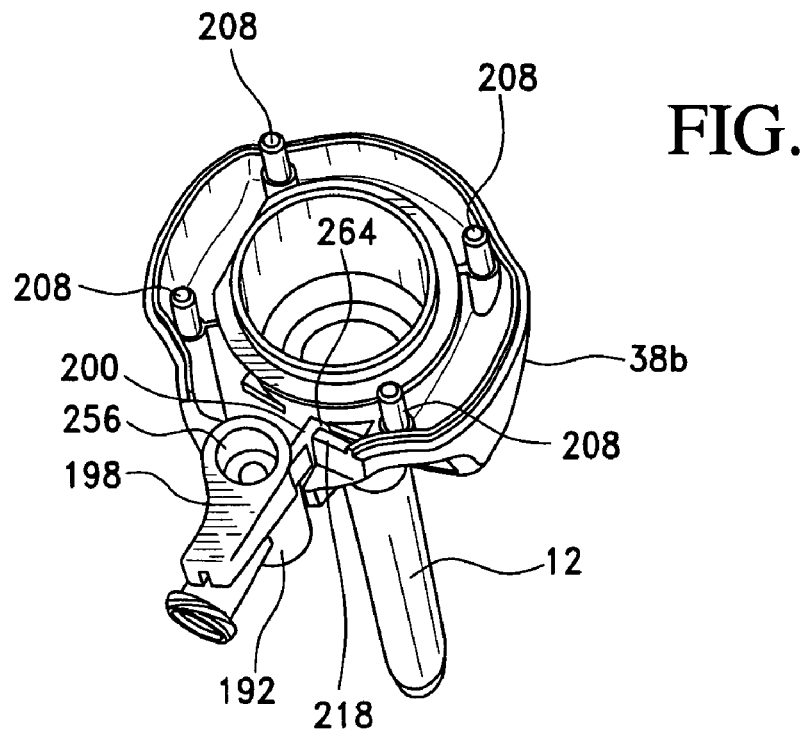
FIG. 19 is an assembled perspective view of the trocar sleeve shown in FIGS. 17 and 18.
Figure 20:
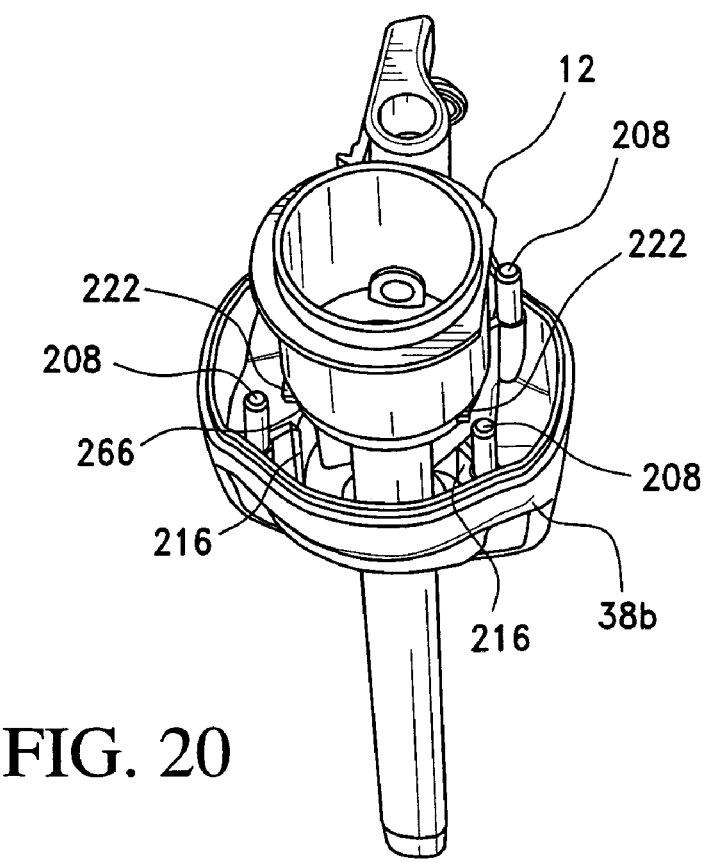
FIG. 20 is a rear perspective view of the trocar sleeve shown in FIGS. 17 and 18.
Figure 21:
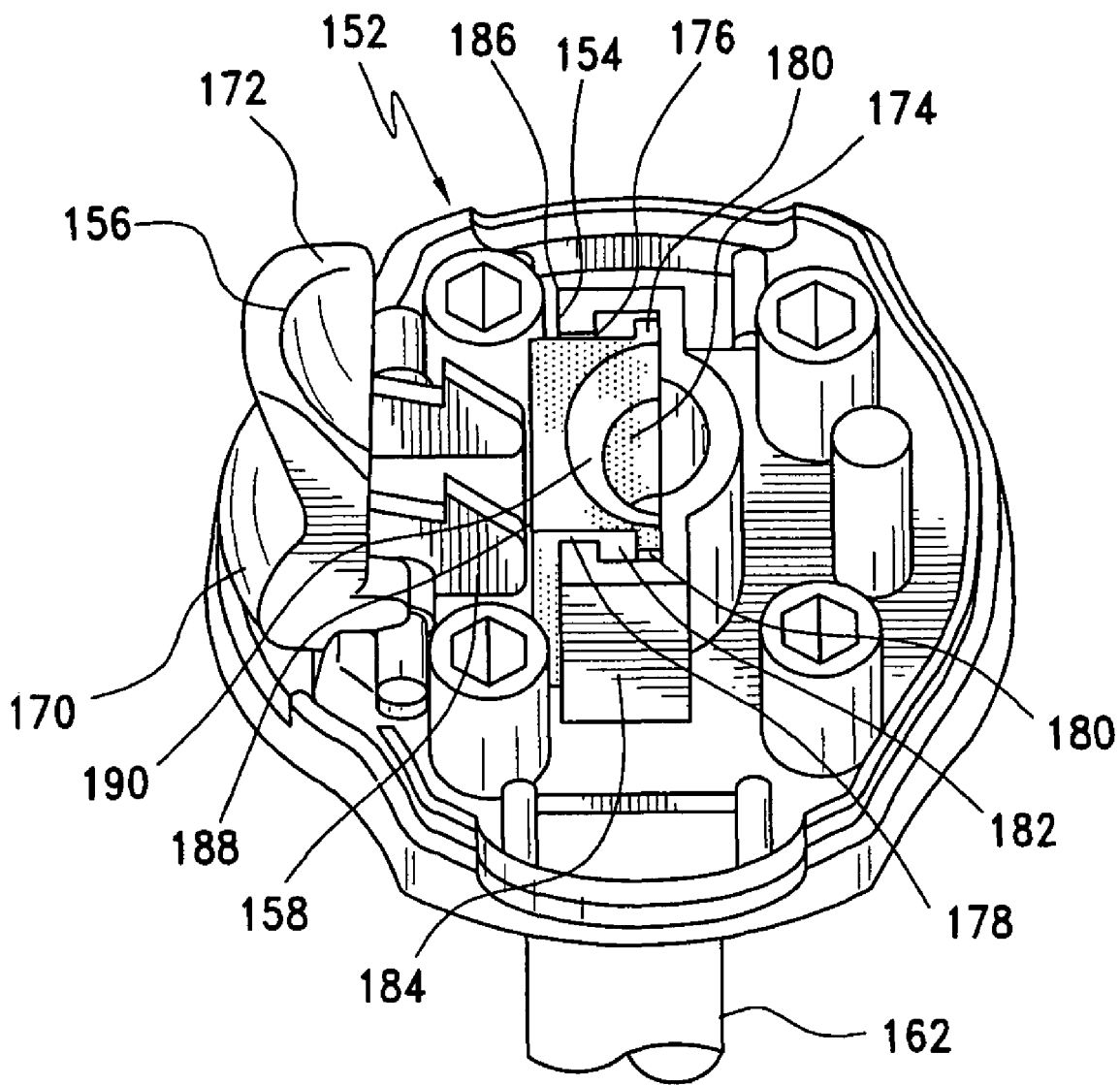
FIG. 21 is a detailed view of the endoscopic lock mechanism.
Figure 22:
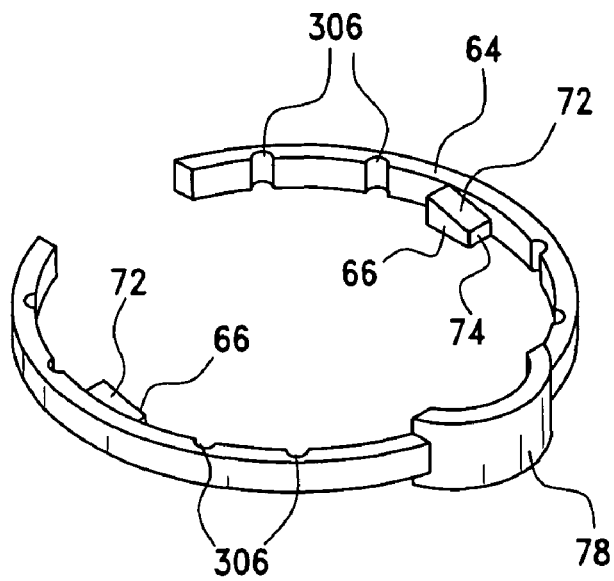
FIG. 22 is a top perspective view of the button latch mechanism.
Figure 23:
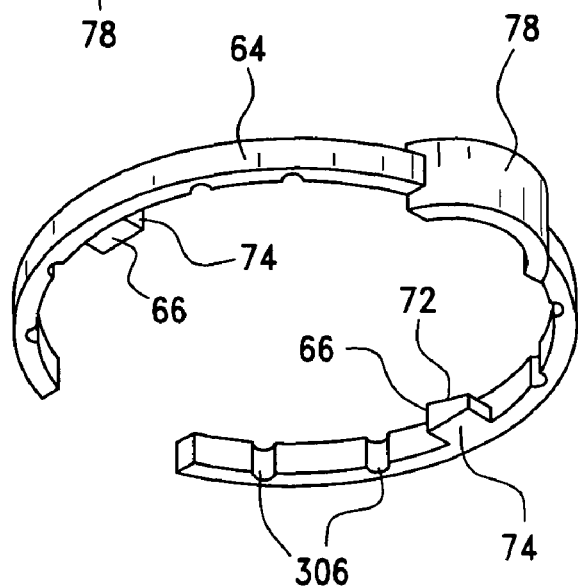
FIG. 23 is a perspective view of the button latch mechanism.
Figure 24:
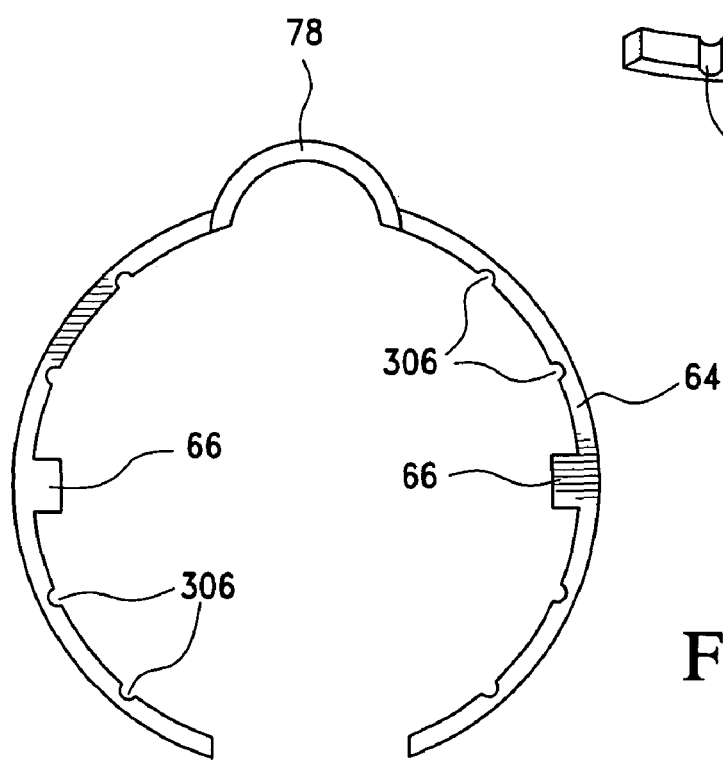
FIG. 24 is bottom view of the button latch mechanism.

As mentioned above, a duckbill seal assembly 32 is housed within the second housing member 38. With reference to FIGS. 14 to 16, the duckbill seal assembly 32 in accordance with a preferred embodiment of the present invention is disclosed. The duckbill seal assembly 32 includes first and second seal bodies 130, 132 extending from a circumferential flange member 134 shaped and dimensioned for mounting within the second housing member 38.

Each of the first and second seal bodies 130, 132 includes an upper surface 136, 138 and a lower surface 140, 142. The upper surface 136, 138 and the lower surface 140, 142 are generally mirror images as the first and second seal bodies 130, 132 maintain a substantially consistent thickness along its entire length with the exception of the reinforcing rib along the upper surface 136, 138.

The first and second seal bodies 130, 132 are mounted within the trocar housing 16 for movement as an instrument is passed therethrough. With this in mind, the proximal end of each of the first and second seal bodies 130, 132 is coupled to the trocar housing 16 via the circumferential flange 134, while the distal ends of the first and second seal bodies 130, 132 intersect to define an abutment face 144. The abutment face 144 is generally positioned within the center of the trocar housing 16 to permit the passage of an instrument therethrough, while in the absence of such an instrument the abutment face 144 is closed via the resilience of the first and second bodies 130, 132 as they are biased under the pressure generated from the body cavity in which the trocar assembly 10 is positioned. For example, biased under the pressure from the abdominal insufflation gas pressure. This pressure causes the duckbill seal assembly 32 to move to a closed position with the distal ends of the first and second seal bodies 130, 132 in contact.

The first and second seal bodies 130, 132 will now be described with reference to the first seal body 130. Those skilled in the art will appreciate that the first and second seal bodies 130, 132 are identical and the following descriptions equally relates to the second seal body 132. The seal body 130 is formed with a first section 148 and a second section 150 angularly oriented relative to each other and a transverse plane 146 extending through the circumferential flange 134. In particular, the transverse plane 146 is substantially perpendicular to the longitudinal axis extending through the duckbill seal assembly 32. The first and second sections 148, 150 extend from a proximal end of the seal body 130 respectively toward a distal end of the seal body 130. As such, the first section 148 is positioned adjacent the proximal end of the seal body 130 adjacent the wall of the circumferential flange 134 and the trocar housing 16. The first section 148 moves only slightly as an instrument is inserted therethrough. The second section 150 is positioned adjacent the distal end of the seal body 130 and adjacent the abutment face 144. The second section 150 freely moves as an instrument is inserted therethrough.

Assuming the transverse plane 146 lies in a horizontal plane, and in accordance with a preferred embodiment of the present invention, the first section 148, which begins at the proximal end of the seal body 130, is oriented at approximately a 30 degree angle relative to the horizontal plane in which the transverse plane 146 lies. The second section 150, which extends to the distal end of the seal body 130, is thereafter oriented at a 45 degree angle relative to the horizontal plane. Those skilled in the art will appreciate that the angles disclosed above in accordance with a preferred embodiment of the present invention may be varied without departing from the spirit of the present invention. The chosen angles are based upon the trade off between the durability of the seal bodies (improves at greater angles as likelihood of an instrument pointedly engaging the seal, i.e. tenting is less likely at greater angles) and the height of the seal (greater angles dictate greater height). For example, it is contemplate the second section 150 may be formed at an angle of approximately 40 degrees to approximately 50 degrees while providing for the many advantages contemplated in accordance with the present duckbill seal assembly 32. The height or profile of the duckbill seal assembly 32 is important as reductions in size allow for improved instrument access because the length of the trocar housing 16 may be consequently made smaller. Smaller housings provide surgeons with greater access within the body cavity and thus are very desirable.

Endoscope Lock Assembly

Figure 3:
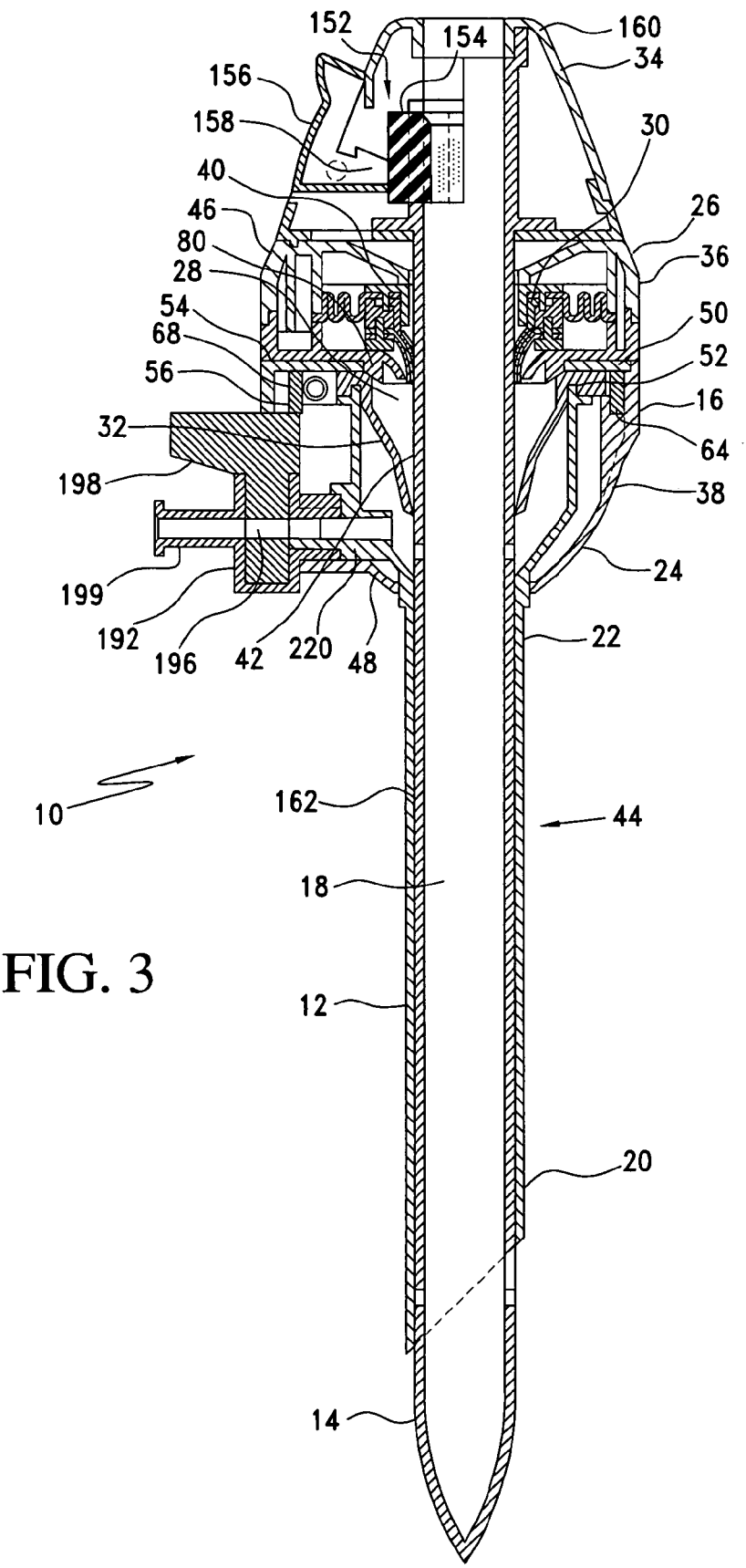
FIG. 3 is a cross sectional view of the trocar assembly shown in FIG. 1.
Figure 4:
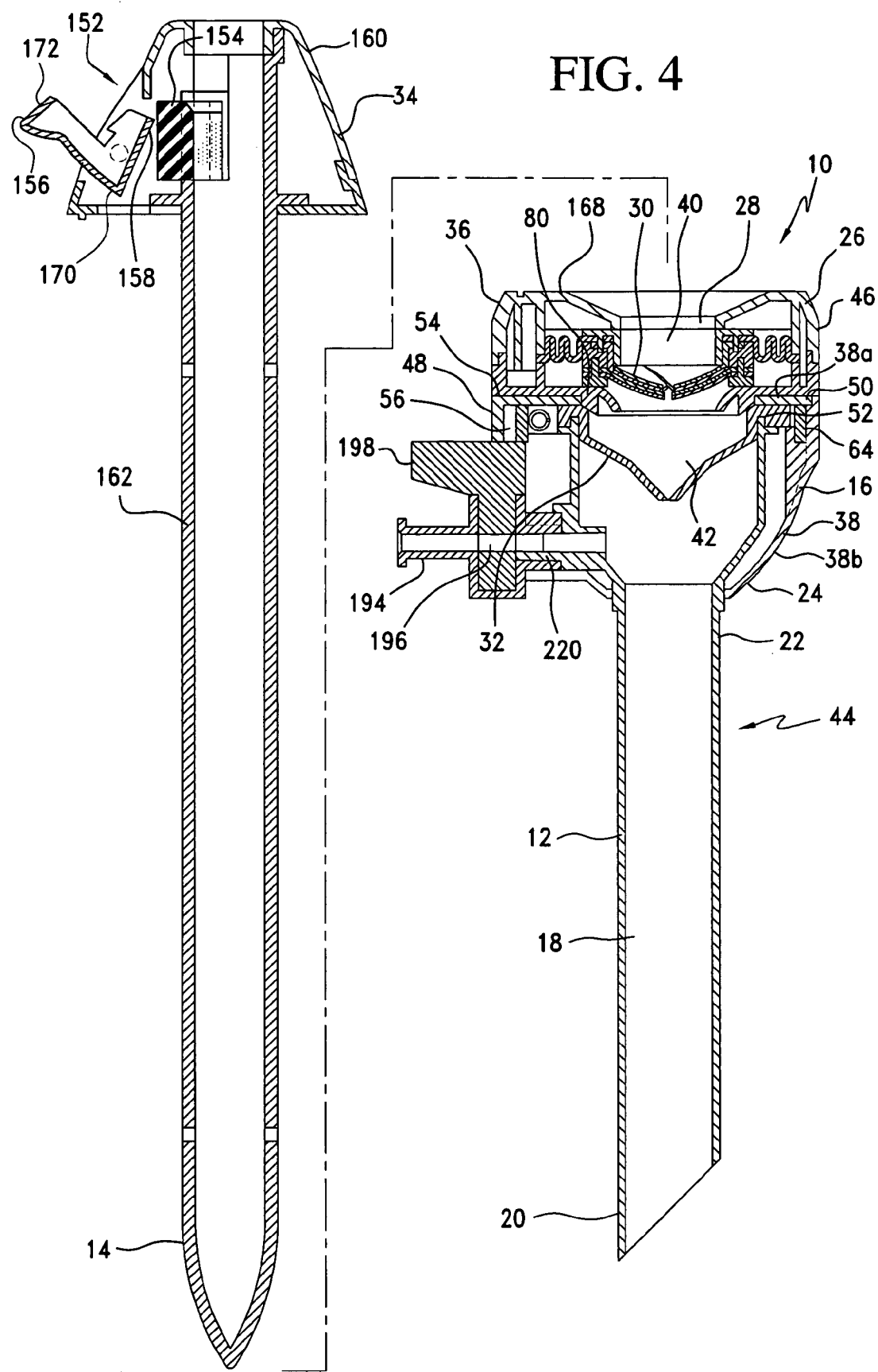
FIG. 4 is an exploded cross sectional view of the trocar assembly shown in FIG. 1.
Figure 5:
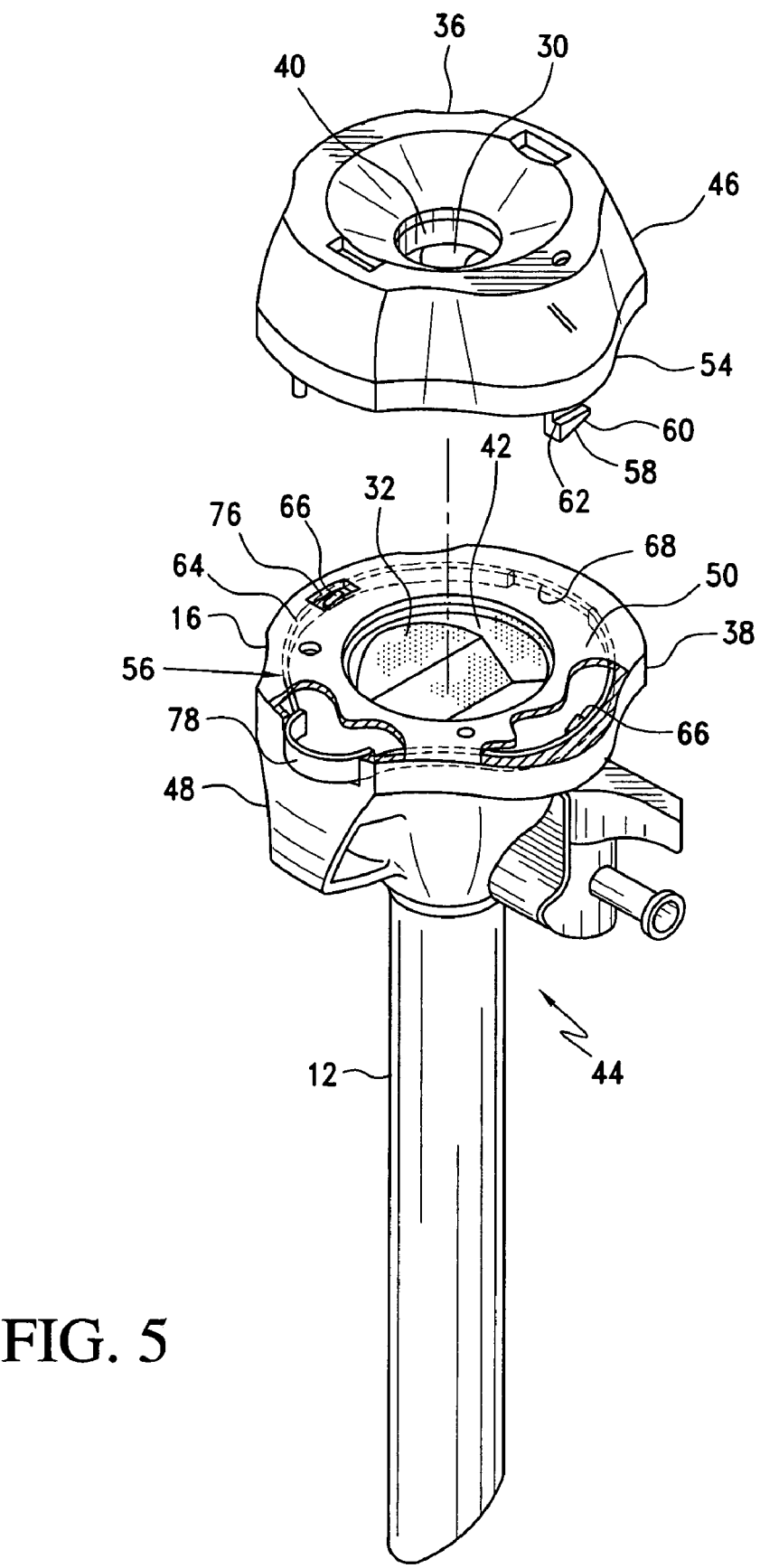
FIG. 5 is a detailed view of the button latch mechanism utilized in accordance with the present trocar assembly.
Figure 6:
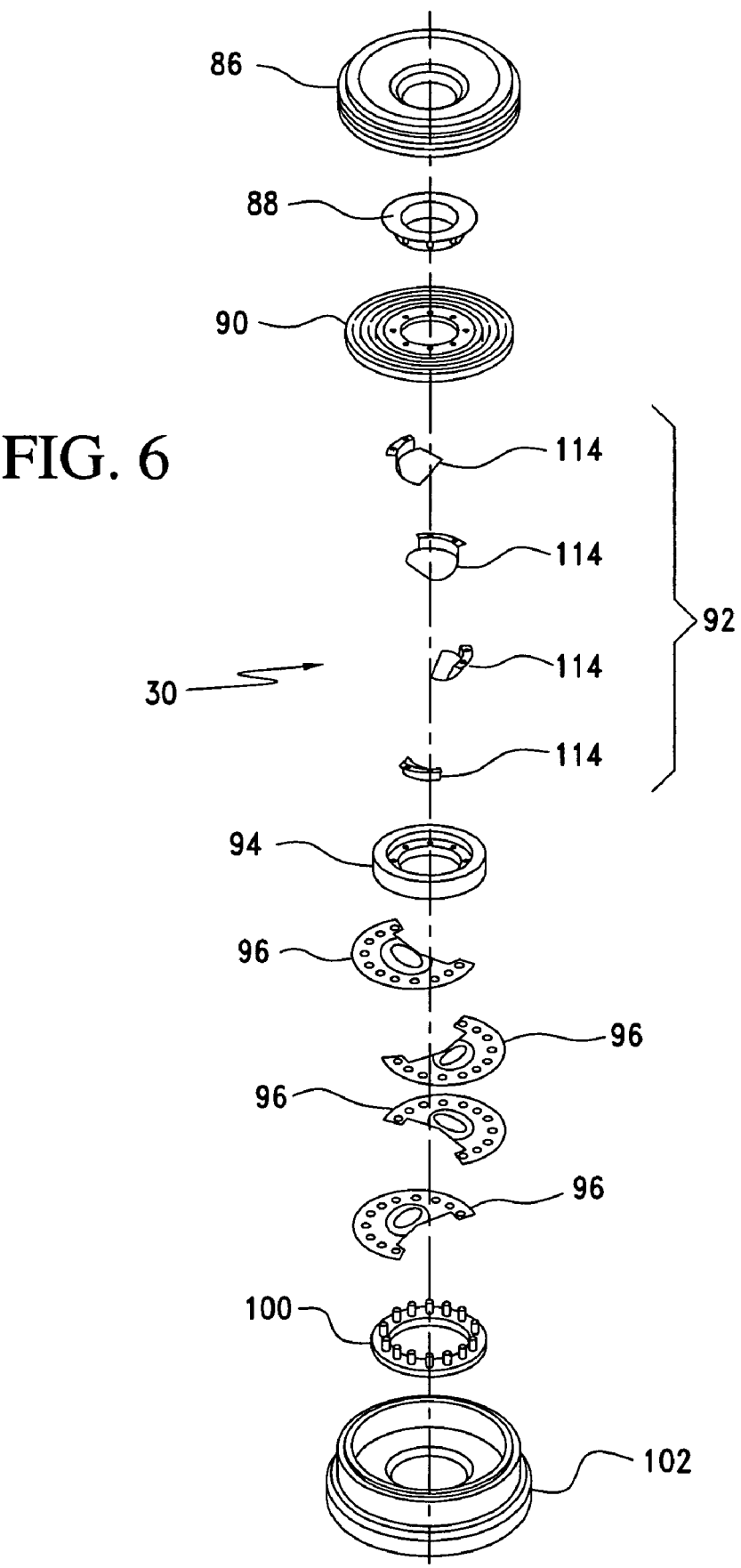
FIG. 6 is an exploded view of the proximal seal assembly in accordance with the present trocar assembly.
Figure 25:
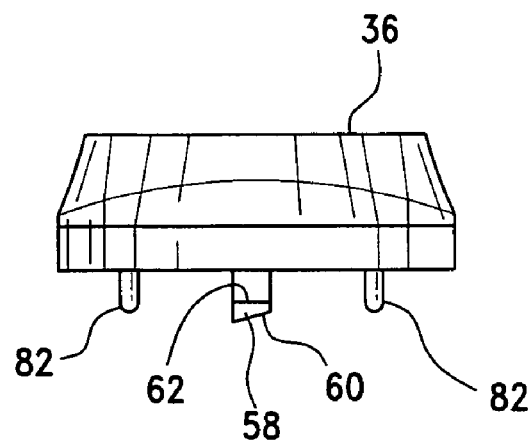
FIG. 25 is a side view of the first housing member showing the detainment legs thereof.
Figure 27:
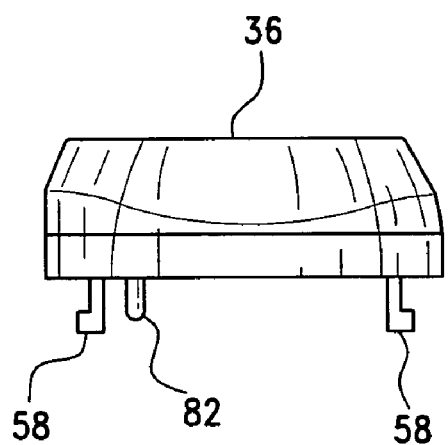
FIG. 27 is a side view of the first housing member.
Figure 26:
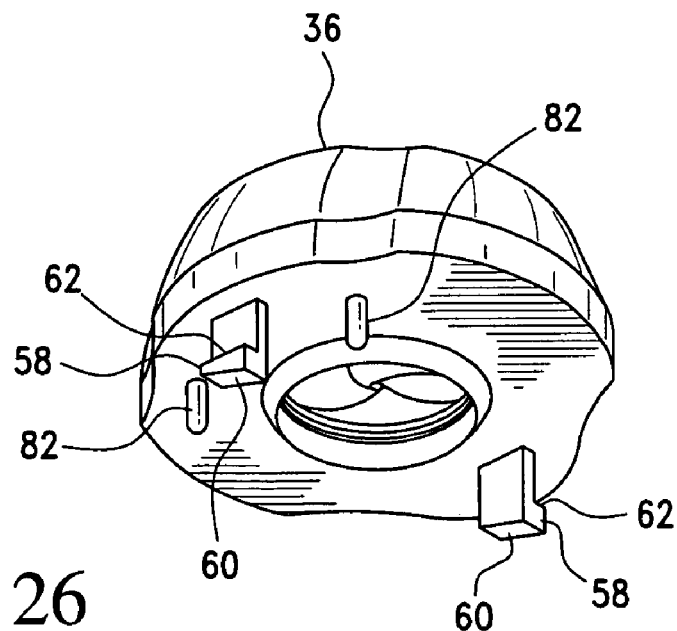
FIG. 26 is bottom perspective view of the first housing member.
Figure 28:
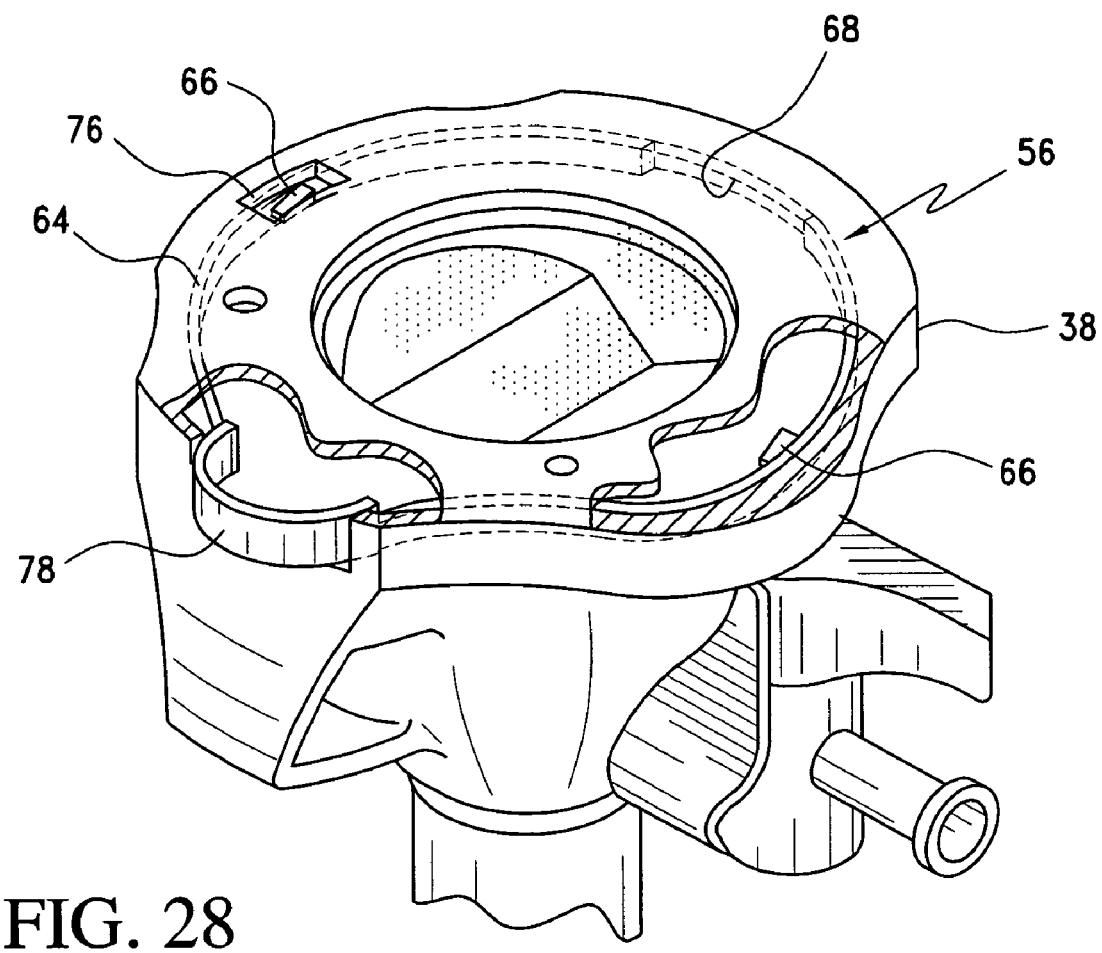
FIG. 28 is side perspective view of the button latch mechanism.

As discussed above in the Background of the Invention, it is often desirable to lock an endoscope in position relative to a trocar assembly 10, in particular, an obturator 14. As such an endoscope lock assembly 152 is provide in accordance with the present invention and is shown in FIGS. 3, 4 and 25. The endoscope lock assembly 152 generally includes a cam mechanism that retains an endoscope within a trocar sleeve 44 and/or obturator 14 during insertion of trocar assembly 10. The mechanism uses a cam to compress an elastomeric block 154 against the endoscope. The elastomeric block 154 then grips the endoscope tightly to prevent undesired motion of the endoscope as the surgeon is visualizing the tissue layers during the trocar assembly insertion. The cam mechanism provides for the ability to retain the endoscope while resisting both torque and axial loads, provides for acceptable endoscope retention after repeated throws of the cam lever 156, provides low ergonomic forces to actuate the cam lever 156, provides for compatibility with a wide range of endoscope sizes, facilitates intuitive use and has a long term shelf life stability.

The cam mechanism that retains the endoscope within a trocar assembly 10 uses a cam surface 158 to compress the elastomeric block 154 against the endoscope. The elastomeric block 154 then grips the endoscope tightly to prevent undesired motion of the endoscope as the surgeon is visualizing the tissue layers during the trocar assembly insertion.

The lock assembly 152 includes a housing 160 having a tube 162 extending therefrom. The tube 162 is aligned with an aperture extending therethrough. The tube is formed with a sharp tip and may be utilized as an obturator in accordance with the present invention. The tube 162 and the aperture are shaped and dimensioned for the extension of an endoscope therethrough. In addition, the tube 162 is shaped and dimensioned to extend through the trocar cannula 12 such that the lock assembly 152, including the tube 162, may be selectively secured to the trocar sleeve 44 for the use of an endoscope.

Attachment of the lock assembly 152 to the trocar first housing member 36 is achieved via mating latches 164, 166 formed on both the underside of the lock assembly housing 160 and the upper surface 168 of the first housing member 36. The latches 164, 166 permit selective attachment and release of the lock assembly 152 to the trocar housing 16. While a specific latching structure is disclosed in accordance with a preferred embodiment of the present invention, other latching structures may be utilized without departing from the spirit of the present invention.

The lock assembly housing 160 includes a camming based locking mechanism. The locking mechanism is composed of a cam lever 156 and an elastomeric block 154. The cam lever 156 includes a first end 170 that is pivotally secured to the housing 160 and a free second end 172 that is adapted for user actuation. In practice, the cam lever 156 may be freely moved between a locking position in which the cam lever 156 is rotated inwardly and a release position in which the cam lever 156 is rotated outwardly.

Camming action in accordance with the present invention is provided by a camming surface 158 adjacent the first end 170 of the cam lever 156. The camming surface 158 is shaped and dimensioned to engage the elastomeric block 154 for selectively locking an endoscope within the lock assembly 152. With regard to the elastomeric block 154, it is housed within the body of the lock assembly housing 160 and includes a forward concave wall 174 shaped and dimensioned for engaging an endoscope passing through the housing aperture. The elastomeric block 154 further includes first and second side walls 176, 178, wherein each side wall 176, 178 includes a notch 180 for engagement with a channel 182 formed within the body of the housing 160. The channel 182 and notch 180 interact to allow lateral movement of the elastomeric block 154 in a manner that is described below in greater detail. The housing 160 further includes upper and lower retaining members 184, 186 for securely preventing upward or downward motion of the elastomeric block 154 within the housing 160. Finally, the elastomeric block 154 includes a rear wall 188 opposite the forward concave wall 174. The rear wall 188 is shaped and dimensioned for engagement with the camming surface 158 of the cam lever 156.

The elastomeric block 154 and the camming surface 158 are shaped to eliminate forceful contact, and in particular eliminate any contact, between the elastomeric block 154 and the camming surface 158 until such a time that an endoscope is positioned with the aperture of the lock assembly housing 160. As will be described below in greater detail, when an endoscope if placed within the aperture of the lock assembly housing 160, the elastomeric block 154 is moved toward the cam lever 156 to such a degree that the elastomeric block 154 comes into proximity of the camming surface 158 for locking of the endoscope within the aperture once the cam lever is actuated.

In practice, the lock assembly 152 is used in the following manner. The elastomeric block 154 sits within the lock assembly housing 160 underneath the cam lever 156, which may be either open or closed during long-term storage. The elastomeric block is purposefully not in contact with the cam lever 156 at this point to avoid any loads on the elastomeric block 154 that could affect the lock assembly's 152 performance after long-term storage. The surgeon then opens the cam lever 156 if it was originally closed. An endoscope is inserted into the lock assembly 154. The endoscope hits a chamfered surface 190 on the concave wall 174 of the elastomeric block 154. This lifts the elastomeric block 154 upward into the proximity of the cam lever 156. The elastomeric block 154 then rests on top of the endoscope for the rest of its use. The cam lever 156 is then actuated, which compresses the compressible scope lock onto the endoscope. The compliance of the elastomeric block 154, along with its high coefficient of friction, allows the lock assembly 152 to be compatible with a wide range of endoscope sizes while minimizing ergonomic force requirements. The elastomeric block 154 is then constrained from excessive sideways or axial motion by surrounding components 182, 184, 186 that limit its motion as axial and torsional loads are applied to the endoscope. This constraint, along with an over-center cam design, prevents the cam lever from accidentally unlocking by itself by accident. After the trocar assembly 10 has been inserted into the patient, the cam lever 156 is then opened and the endoscope is removed. The elastomeric block 154 then returns to its original position in the lock assembly 152 if the surgeon wishes to reinsert the endoscope at a later time. The compliant elastomeric block 154 has sufficient rigidity to return to its original shape after the load from the cam lever 156 has been removed, thus providing acceptable endoscope retention force over the course of multiple lever actuations.

Trocar Sleeve and Stop-Cock Valve Construction

As mentioned above, the trocar sleeve 44 is composed of a trocar housing 16 and a trocar cannula 12 extending from the trocar housing 16. The trocar assembly 10 also includes a stop-cock valve 192 for allowing and preventing the passage of an insufflation fluid, e.g. carbon dioxide, through flexible tubing into a portion of the trocar housing 16 and the trocar cannula 12.

With reference to the figures, the trocar cannula 12 and the trocar housing 16 are mechanically interfitted to form the trocar sleeve 44. At least a portion of the trocar cannula 12 sits within a second housing member base 38*b* of the second housing member 38 with a second housing member cover 38*a* sitting over the trocar cannula 12 for securing the at least a portion of the trocar cannula 12 within the second housing member base 38*b*.

The trocar cannula 12 is sized so that when the trocar obturator 14 extends completely through it and beyond, insufflation fluid, which passes through the stop-cock valve 192 and the trocar housing 16, can pass through an annular opening created between the trocar cannula 12 and the trocar obturator 14 by the slightly greater size of the internal diameter of the trocar cannula 12 in relation to the outer diameter of the hollow shaft of the trocar obturator 14.

The present invention provides a mechanism for mechanically assembling the trocar cannula 12, trocar housing 16 and stop-cock valve 192 without the need for adhesive and/or curing techniques. In particular, the second housing member 38 of the trocar housing 16, trocar cannula 12 and stop-cock valve 192 are formed as separate components that may be assembled in a convenient and reliable manner.

More particularly, and with reference to FIGS. 17, 18, 19 and 20, a preferred embodiment of the mechanically assembled trocar sleeve 44 is disclosed. The trocar sleeve 44, when, fully assembled, comprises a stop-cock valve 192, a second housing member 38 composed of a second housing member cover 38*a* and a second housing member base 38*b*, and a trocar cannula 12. The various components of the trocar sleeve 44 are mechanically assembled by interfitting the components in a manner that is described below in greater detail. Briefly, the trocar cannula 12 fits within the second housing member base 38*b* with the stop-cock valve 192 positioned therebetween. The second housing member cover 38*a* fits over the stop-cock valve 192, second housing member base 38*b* and trocar cannula 12 to retain the various components together and provided a surface upon which the first housing member 36 may be selectively mounted.

With regard to the specific components making up the trocar sleeve 44, and in accordance with a preferred embodiment of the present invention, the stop-cock valve 192 includes alignment wings 194, a flow opening 196, and a valve lever 198. The valve lever 198 includes a stop latch 200. The second housing member cover 38*a* includes a hexagonal bore 202, a cover rim 204, and a second housing member cover seal 206. The second housing member base 38*b* includes friction posts 208, vanes 210, a housing rim 212, a clearance 214 for the stop-cock valve 192 and alignment wings 194. The second housing member base 38*b* further includes alignment ribs 216 and a latching face 218. The trocar cannula 12 includes an inlet nipple 220, alignment tabs 222, and a housing seal 224.

In practice, the stop-cock valve 192 is inserted into the clearance 214 of the second housing member base 38*b*. The trocar cannula 12 inserts through the opening of the second housing member base 38*b*. The alignment tabs 222 abut the vanes 210 securing the trocar cannula 12 in a desired orientation with respect to the second housing member base 38*b* once the trocar cannula 12 is inserted into the second housing member base 38*b*.

The cover rim 204 mates with the housing rim 212. The cover rim 204 also serves to hold the valve lever 198 on the stop-cock valve 192 as well as hold the stop-cock valve 192 with the valve lever 198 in position.

The valve lever 198, in a maximum flow allowance position, i.e., fully open, has the stop latch 200 abut onto the latching face 218 of the second housing member base 38*b*. This means an operator of the valve lever 198 can sense when the valve lever 198 is in a fully open position by abutting latch face 218 and the valve lever 198 stays in the fully open position. The operator does not have to guess that the valve lever 198 is in the fully open position, and the valve lever 198 stays in the fully open position.

The construction of the trocar assembly 44 eliminates the need for adhesives to join the stop-cock valve 192 and the second housing member cover 38*a*, and the second housing member base 38*b* and the trocar cannula 12. This is an advantage over prior art.

the stop-cock valve 192 is mechanically coupled to the trocar sleeve 44 via tapered surfaces shaped and dimensioned for frictional engagement. As such, the outlet tube 250 of the stop-cock valve 192 is formed with a tapered lock surface along the exterior of its distal end. Similarly, the trocar cannula 12 is formed with an inlet nipple 220, adapted for secure coupling with the tapered lock surface of the outlet tube 250 of the stop-cock valve 192. The tapered lock mechanical feature includes a self holding 2.0 degrees +/−1.0 degrees angle, which is firmly seated into the trocar housing inlet nipple 220. The result of this mechanical connection is considerable frictional resistance to rotational and linear pull out forces.

The mechanical lock discussed above may be enhanced by the provision of a dual redundancy feature. For example, the taper lock feature may be provided with a post and hex socket interlock, tongue and groove interlock and/or a snap fit interlock.

In addition, and in accordance with the embodiment described above with reference to FIG. 18, rotation of the stop-cock valve 192 is minimized by the inclusion of a retaining pin 204 located on the second housing member cover 38a that extends downwardly into the aperture 256 formed in the top of the valve lever 198. The retaining pin 204 stabilizes the stop-cock valve 192 and prevents rotation as the valve lever 198 of the stop-cock valve 192 is actuated.

As mentioned above, the trocar sleeve includes a stop-cock valve 192. The stop-cock valve 192 is mounted within a recess formed in the trocar sleeve 44. As such, the stop-cock valve 192 recessed within the outer surface of the second housing member base 38b, and ultimately the trocar housing 16. The valve lever 198 is further positioned above the body of the stop-cock valve 192; that is, the valve lever 198 used in actuating the stop-cock valve 192 is positioned on the top surface of the stop-cock valve 192 instead of underneath as with trocar assemblies currently in the marketplace. By positioning the valve lever 198 above the recessed stop-cock valve 192, the present trocar assembly 10 provides for the removal of the stop-cock valve 192 from a potentially obstructing view while simultaneously placing the valve lever 198 in a highly accessible position.

Several advantages are achieved by recessing the stop-cock valve 192 within the body of the trocar sleeve 44. First, this orientation minimizes the obstructions caused by users gripping the stop-cock valve 192 of the trocar assembly 10 for insertion. A more comfortable grip is, therefore, provided, as the stop-cock valve 192 no longer protrudes from the surface of the trocar housing 16. The present low profile stop-cock valve 192 structure further helps to prevent compromising desired hand positions. The present stop-cock valve 192 orientation also helps to prevent accidental manipulation during procedures. Accidental manipulation by movement of the trocar sleeve 44 into contact with a patient is a common occurrence that results in desufflation of the body cavity and can lead to frustrating and even dangerous situations when the medical professional's field of view is compromised.

Controlled rotation of the valve lever 198 of the stop-cock valve 192 is achieved through the positioning of the stop-cock valve 192 within a recess formed in the trocar sleeve 44, more specifically, the trocar housing 16. Specifically, and with reference to FIGS. 17, 18, 19 and 20, the valve lever 198 of the stop-cock valve 192 includes a stop latch 200 located on the valve 198 which provides tactile feedback as to when the valve lever 198 is in the open position, i.e., the through holes located on the valve lever 198 and valve body 199 are aligned. The design feature resembles a cantilever beam located on the end of the valve lever 198 opposite the user end.

As the valve lever 198 is rotated from the closed position to the open position within the trocar assembly 10, the cantilever rotational stop latch 200 contacts the trocar housing 16 providing tactile feedback that the valve lever 198 is in the fully opened position. In the fully opened position, the valve lever 198 and valve body 199 through holes are aligned allowing for optimal $CO_2$ flow.

The cantilever rotational stop latch 200 feature provides the surgeon with tactile feedback to ensure that the stop-cock valve 192 is in the open position. This will provide the optimal flow of $CO_2$ flow throughout the surgical case.

As those skilled in the art will appreciate, control of the valve lever 198 via the cantilever rotational stop latch 200 helps in alignment of the stop-cock valve 192 through hole 196. Misalignment of through holes 196 is commonly caused by lack of tactile feedback to the surgeon that the valve lever 198 is in the fully opened position.

In addition, a strengthening gusset 264 is located on the backside of the cantilever rotational stop latch 260 to prevent over-rotation of the valve lever 198 by bending the valve lever 198. This can be seen in FIGS. 17 and 18. Over-rotation would create misalignment of the through holes.

As those skilled in the art will certainly appreciate, the design described above offers many advantages over prior art assemblies. The separate trocar cannula 12 design described above provides for interchangeable outer housing capabilities. As such, the industrial design outside shape can be readily changed and updated without changing the internal structure of the trocar sleeve. In addition, assembly of the trocar cannula 12 to the trocar housing 16 joint system eliminates the need for ultrasonic welding. The present assembly method makes the device stronger by molding the trocar cannula 12 in one part. As those skilled in the art will certainly appreciate, prior designs utilized ultrasonic weld joints to assemble the trocar cannula 12 to the trocar housing 16. The present assembly structure eliminates the use of such joints and, therefore, provides no opportunity for failure of the ultrasonic weld joints.

In addition, the trocar housing 16 is provided with crush ribs 266 along its internal surface. These crush ribs 266 center the trocar cannula 12 within the trocar housing 16. They also take up small variations in tolerances making the size of the trocar cannula 12 during manufacture less important and allowing for inherent variations during the molding process.

The crush ribs 266 further prevent rotation of the trocar cannula 12 within the trocar housing 16. This is achieved as the crush ribs 266 extend into the sides of the trocar cannula 12 thereby preventing relative rotation between the trocar cannula 12 and the trocar housing 16.

Since the trocar housing 16 and trocar cannula 12 are rather simple in construction, the molding process is simplified by eliminating excessive core details on the injection mold tool. In addition, assembly of the system is easy as compared to prior designs as all of the components making up the sleeve assembly can be assembled in a top down manner.

As to the stop-cock valve 192, the taper lock with dual redundant locking features helps to prevent the stop-cock valve 192 from falling off the trocar sleeve 44. In addition, the taper lock provides an airtight assembly without the use of adhesive or welding. In addition, the stop-cock valve 192 is provided with various lock surfaces preventing rotation of the stop-cock valve 192, for example, post and socket, tongue and groove, wings on ribs, etc. In addition to the taper lock features, the wings are trapped behind the trocar housing 16, eliminating the possibility for removal of the stop-cock valve 192 from the trocar sleeve 44. In addition, crush ribs 266 are utilized in holding the wings tight onto the trocar cannula 12. Finally, the low profile stop-cock valve 192 structure with a valve lever 198 positioned above the stop-cock valve 192 allows for alignment of the stop-cock valve 192 to provide optimal air flow and offers users a tactile feedback for optimizing alignment.

While the preferred embodiments have been shown and described, it will be understood that there is no intent to limit the invention by such disclosure, but rather, is intended to cover all modifications and alternate constructions falling within the spirit and scope of the invention as defined in the appended claims.

The invention claimed is:

1. A trocar housing for a trocar assembly, comprising:
 a first housing member selectively coupled to a second housing member, wherein the first and second housing members include aligned apertures shaped and dimensioned for passage of an instrument therethrough;
 a button latch mechanism selectively coupling the first housing member and the second housing member, the button latch mechanism including:
 a resilient latching member positioned within an annular groove formed in the second housing member, the latching member circumferentially sliding in the annular groove about a central axis of the first and second housing members for selectively coupling the first and second housing members, the latching member including a detainment pin;
 at least one arm downwardly extending from the first housing member; and an aperture formed in the second housing member through which the arm is passed to engage the detainment pin for engagement of the first and second housing members, the aperture being only slightly larger than the arm to prevent bending of the arm by the interaction of the at least one arm with the detainment pin.

2. The trocar housing according to claim 1, wherein the central axis about which the latching member slides is substantially aligned with an axis extending through the aligned apertures of the first housing member and the second housing member.

3. The trocar housing according to claim 1, wherein the latching member is a ring mounted within the second housing member.

4. The trocar housing according to claim 3, wherein the detainment pin includes a pin camming surface and the arm includes an arm camming surface, and the pin camming surface interacts with the arm camming surface for selective engagement of the ring and the arm.

5. The trocar housing according to claim 3, wherein the ring is spring biased.

6. The trocar housing according to claim 5, wherein the ring is composed of a resilient material.

7. The trocar housing according to claim 6, wherein the ring is C-shaped and is positioned within the second housing member such that a spring force is maintained within the ring.

8. The trocar housing according to claim 1, further including an alignment pin ensuring proper orientation of the first housing member relative to the second housing member.

* * * * *